(12) United States Patent
Keidar et al.

(10) Patent No.: US 8,377,117 B2
(45) Date of Patent: Feb. 19, 2013

(54) ACTIVE HOLDER FOR ANNULOPLASTY RING DELIVERY

(75) Inventors: Yaron Keidar, Haifa (IL); Vaso Adzich, Santa Ana, CA (US); Dan Rottenberg, Haifa (IL); Boaz Manash, Givat Ada (IL); Alon Nahshon, Pardes Hanna (IL)

(73) Assignee: Edwards Lifesciences Corporation, Irvine, CA (US)

( * ) Notice: Subject to any disclaimer, the term of this patent is extended or adjusted under 35 U.S.C. 154(b) by 976 days.

(21) Appl. No.: 12/206,604

(22) Filed: Sep. 8, 2008

(65) Prior Publication Data

US 2009/0093877 A1    Apr. 9, 2009

Related U.S. Application Data

(60) Provisional application No. 60/970,872, filed on Sep. 7, 2007.

(51) Int. Cl.
  *A61F 2/24* (2006.01)
  *A61F 2/06* (2006.01)
(52) U.S. Cl. ........................ 623/2.11; 623/2.36; 606/148
(58) Field of Classification Search ................ 623/2.11, 623/2.36–23.7; 606/108, 144, 148
  See application file for complete search history.

(56) References Cited

U.S. PATENT DOCUMENTS

| | | | |
|---|---|---|---|
| 5,350,420 A | 9/1994 | Cosgrove et al. | |
| 5,522,884 A * | 6/1996 | Wright | ........................ 623/2.11 |
| 566,991 A | 11/1996 | Krueger | |
| 571,395 A | 9/1997 | Sanders | |
| 557,807 A | 2/1998 | Garrison | |
| 571,872 A | 2/1998 | Sterman | |
| 5,788,689 A | 8/1998 | Allan et al. | |
| 581,410 A | 9/1998 | Wallner | |
| 5,814,097 A | 9/1998 | Sterman et al. | |
| 587,148 A | 2/1999 | Ovil | |
| 597,203 A | 10/1999 | Garrison | |
| 6,319,280 B1 | 11/2001 | Schoon | |
| 645,105 A1 | 9/2002 | Stevens | |
| 656,480 A1 | 5/2003 | Garrison | |
| 2006/0282162 A1 * | 12/2006 | Nguyen et al. | ............... 623/2.11 |
| 2008/0188873 A1 * | 8/2008 | Speziali | ........................ 606/144 |

FOREIGN PATENT DOCUMENTS

| | | | |
|---|---|---|---|
| GB | 2108393 A | 5/1983 | |
| WO | 9418909 A2 | 9/1994 | |
| WO | 9530386 A1 | 11/1995 | |

* cited by examiner

*Primary Examiner* — Kathleen Sonnett
*Assistant Examiner* — Sarah W Aleman
(74) *Attorney, Agent, or Firm* — AnneMarie Kaiser; Guy Cumberbatch

(57) ABSTRACT

An active annuloplasty ring holder having a template that can be folded or pivoted to the side allowing the template to align longitudinally with the handle and enter the patient's chest through a small incision. The holder may include a mechanism to remotely detach sutures fastening the ring to the holder, thereby detaching the ring while avoiding the risk associated with introducing a scalpel into the operating field. A detachment mechanism may include a movable pin actuated by a pull wire that releases a plurality of holding sutures, or a hot wire, knives, or pull wire that severs the sutures. The holder may have a built-in light source for better visualization of the ring inside the heart. The holder may also have an optical means of visualizing the inside of the heart from the proximal end of the handle.

33 Claims, 19 Drawing Sheets

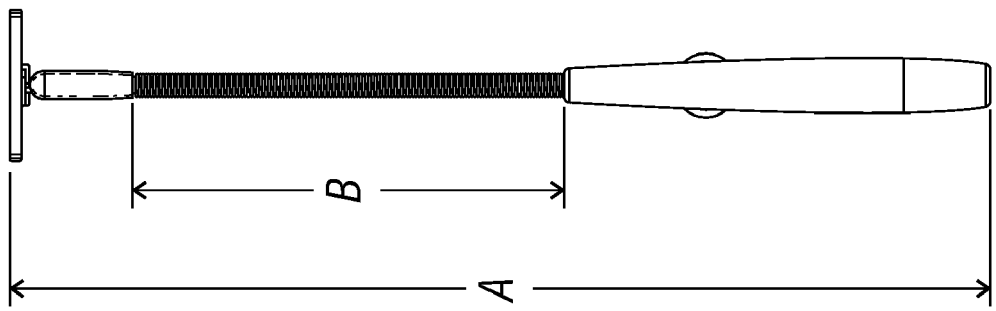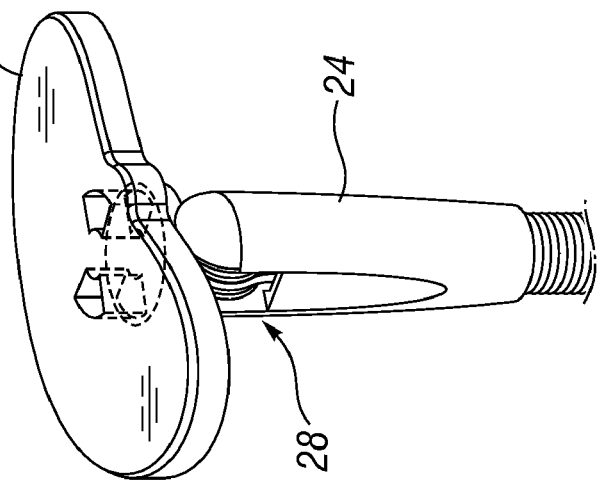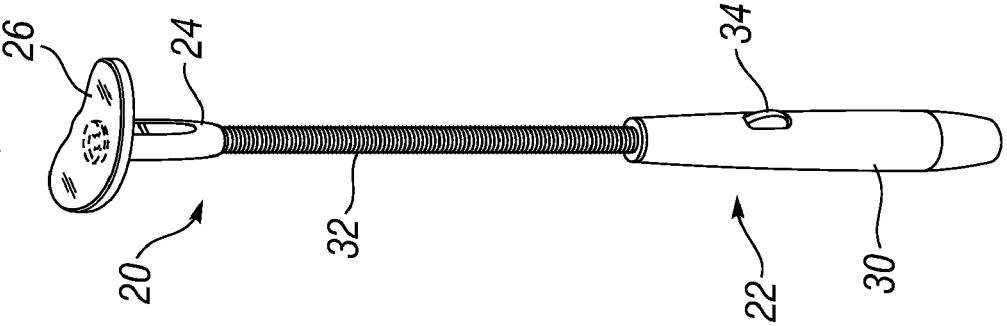

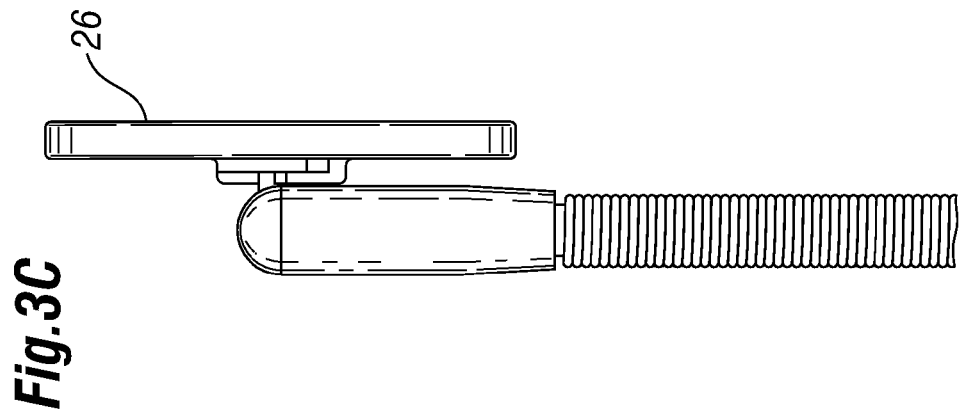
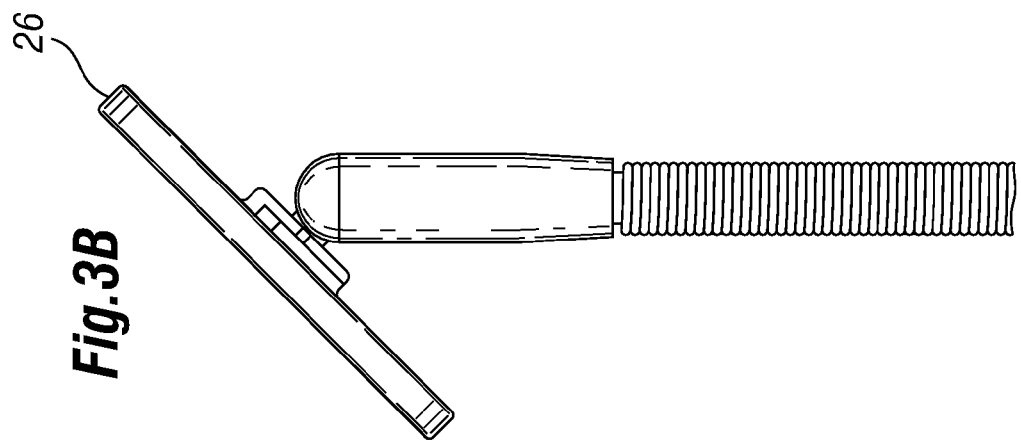
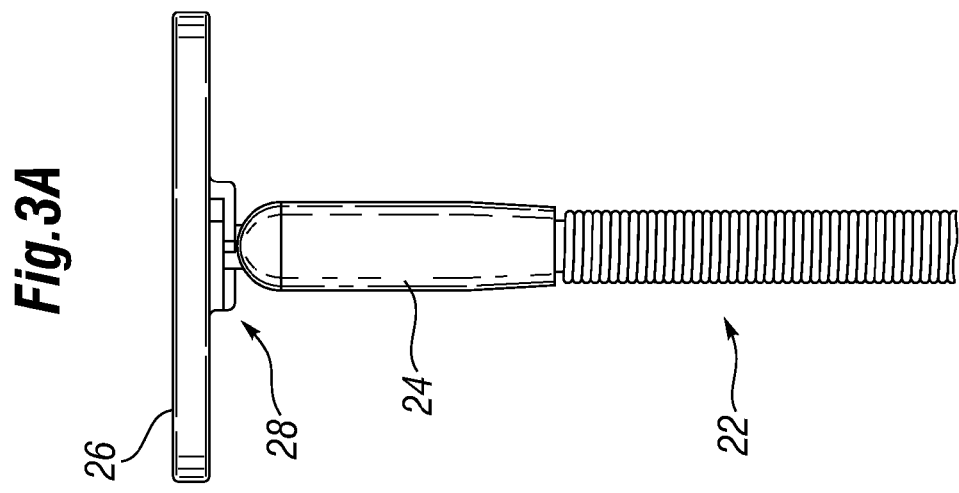

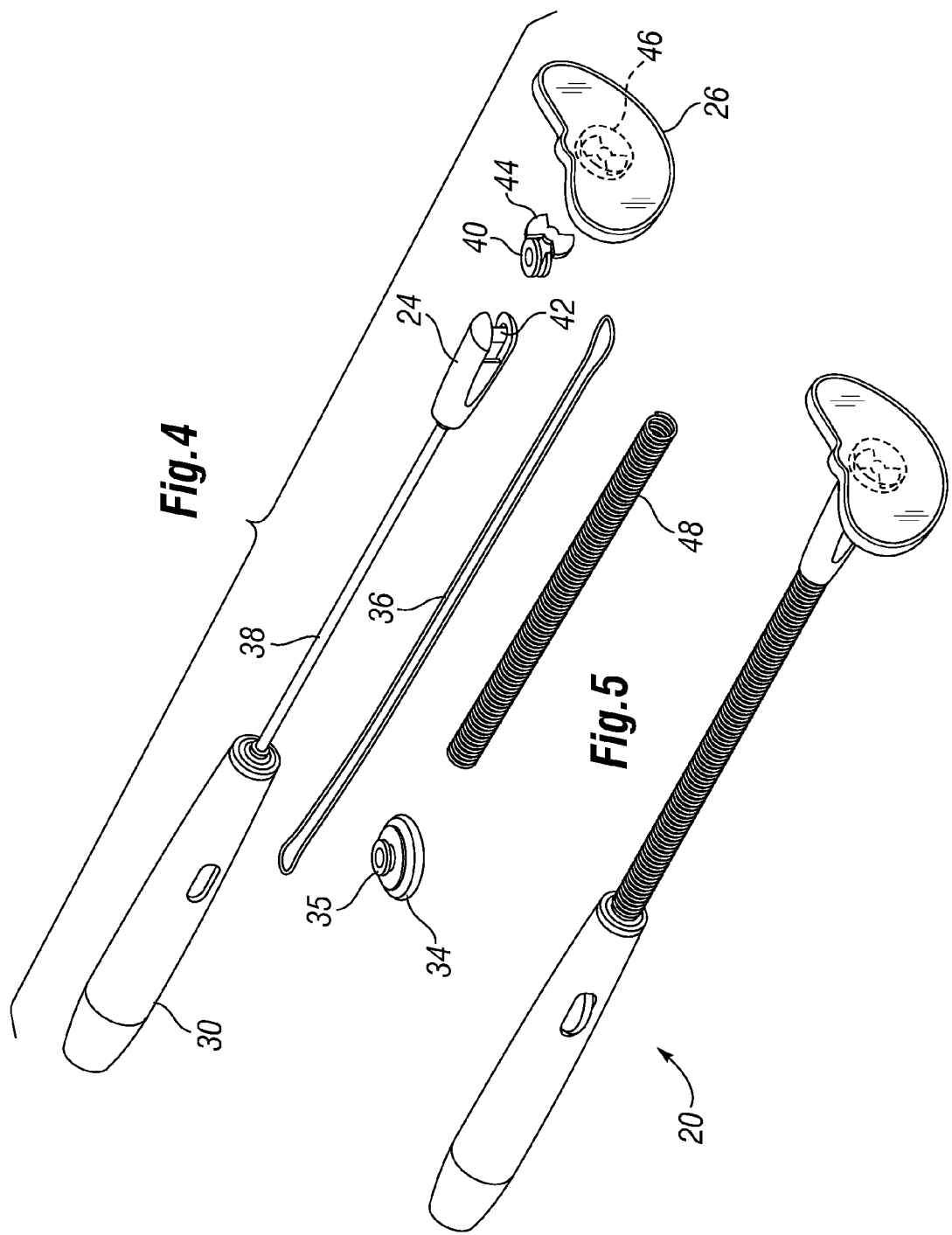

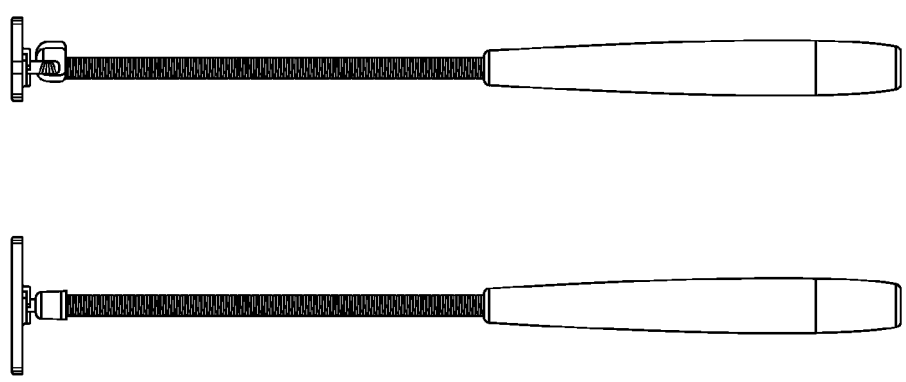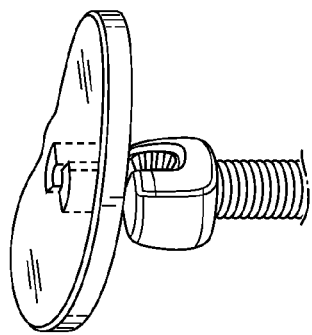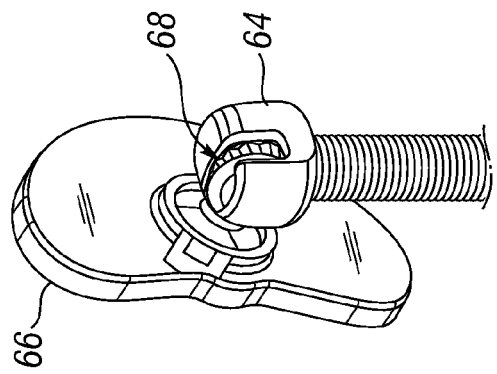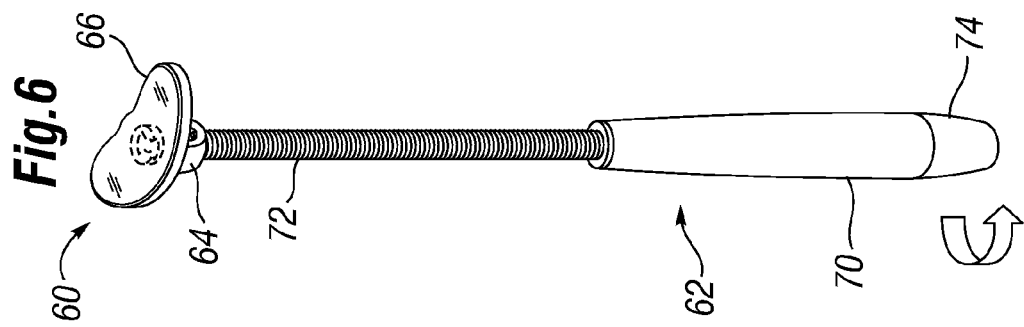

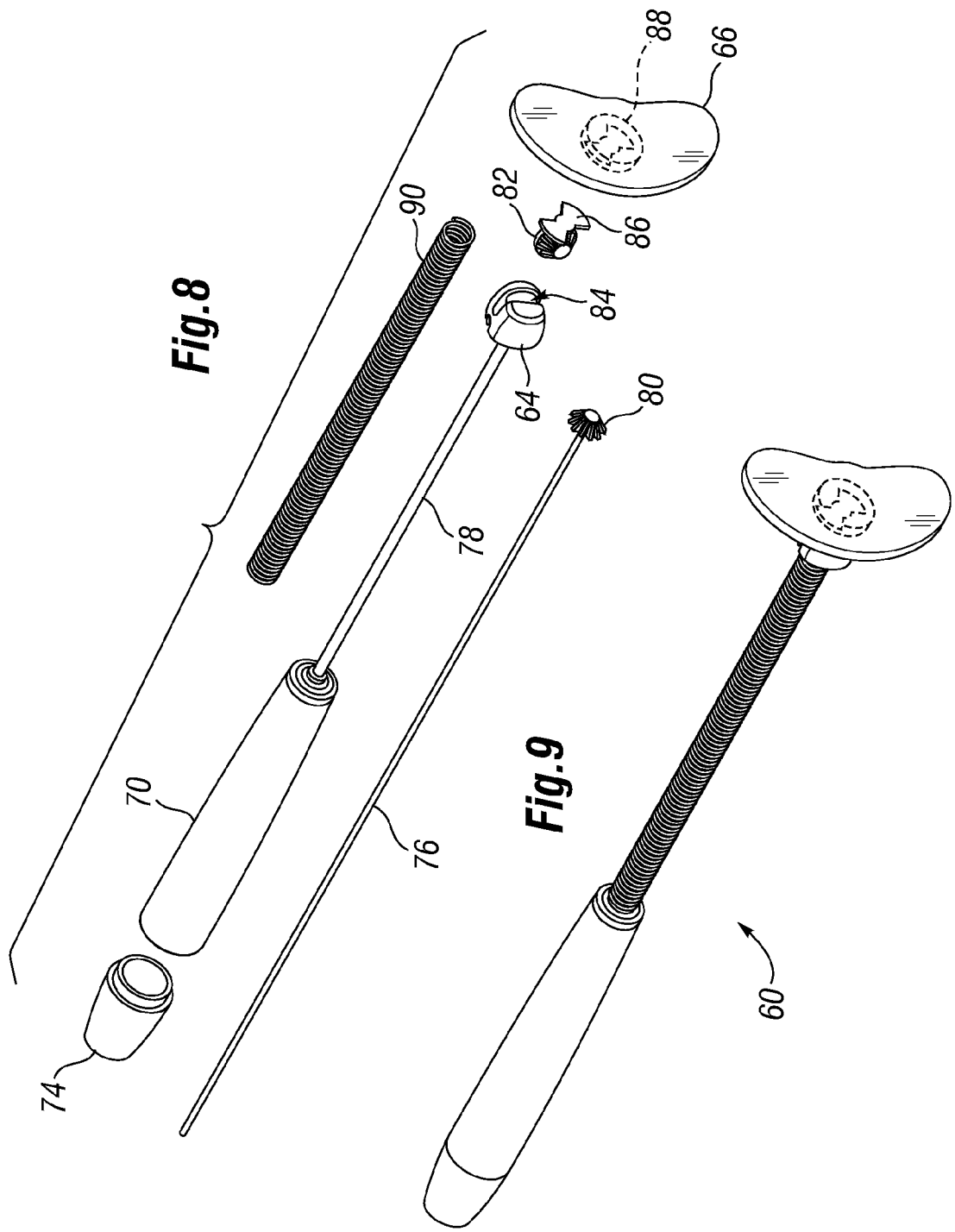

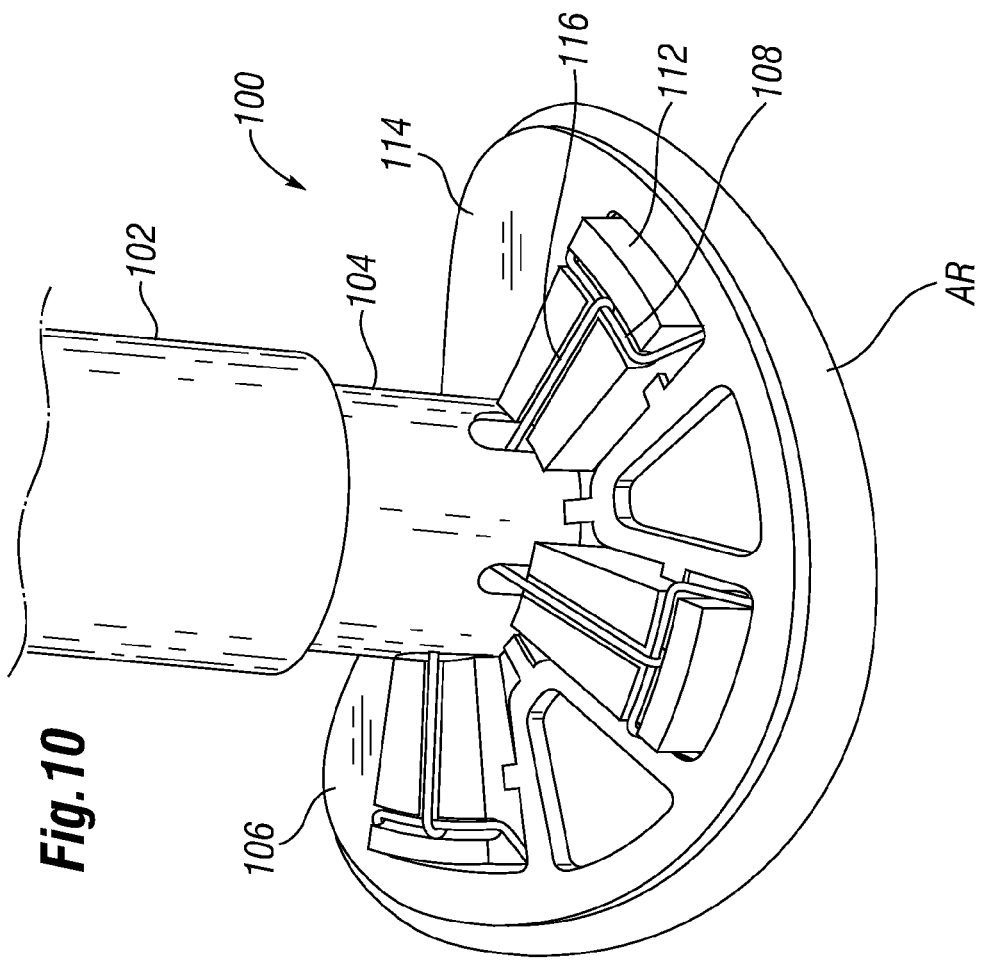
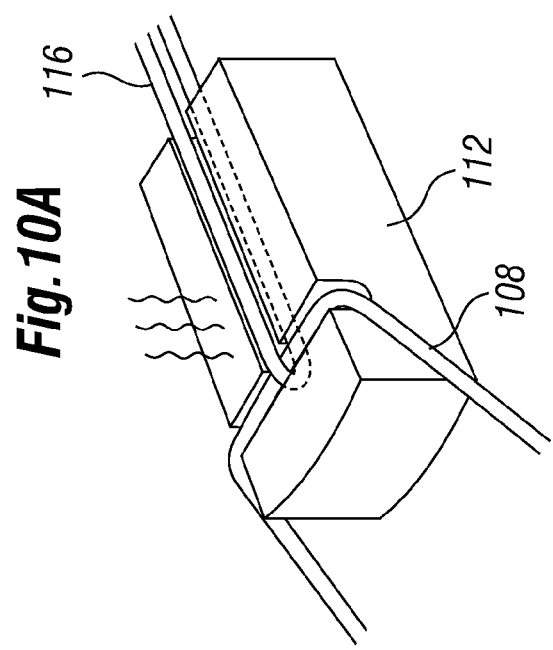

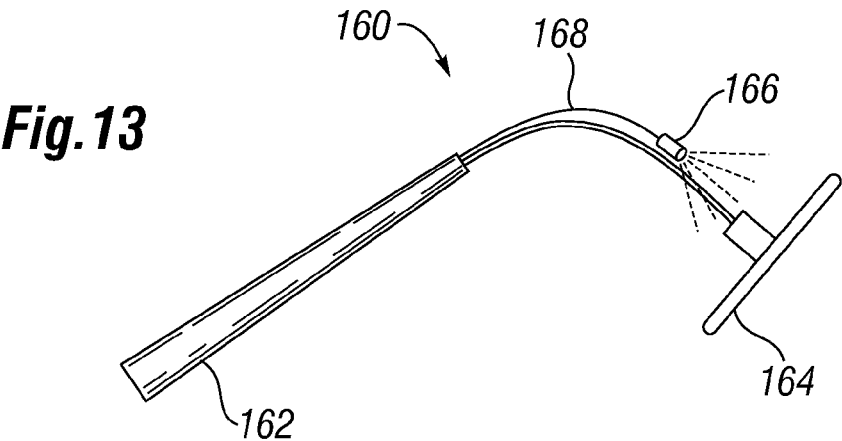
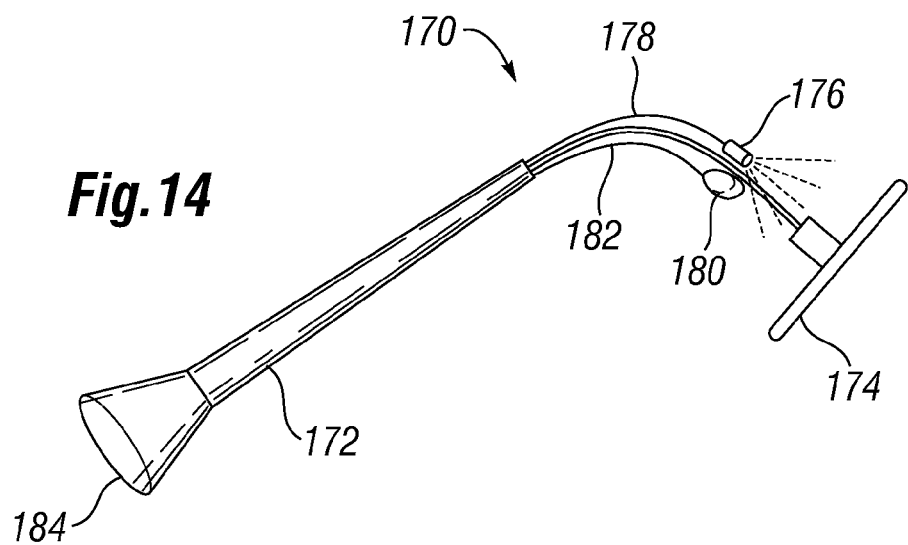

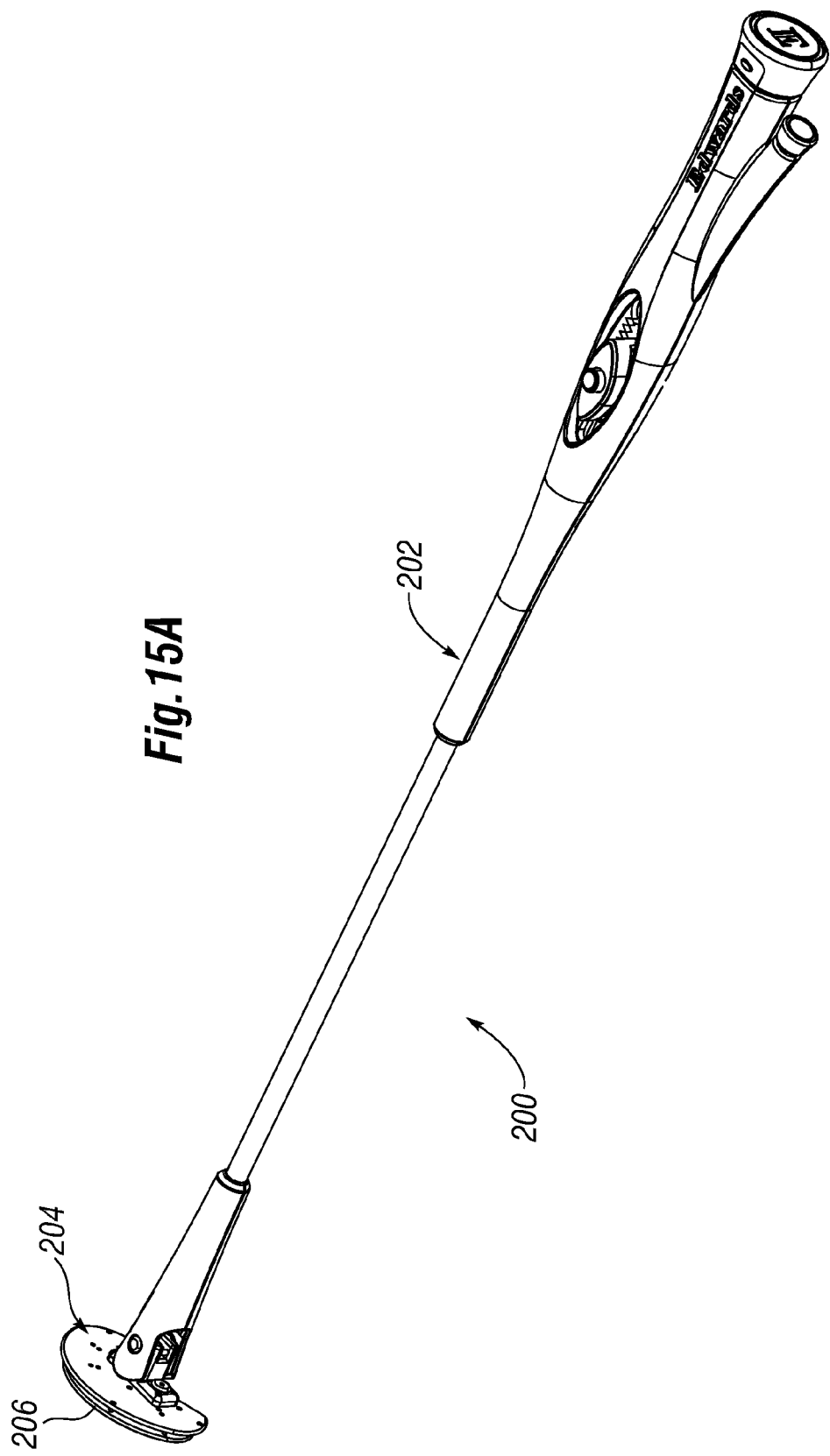

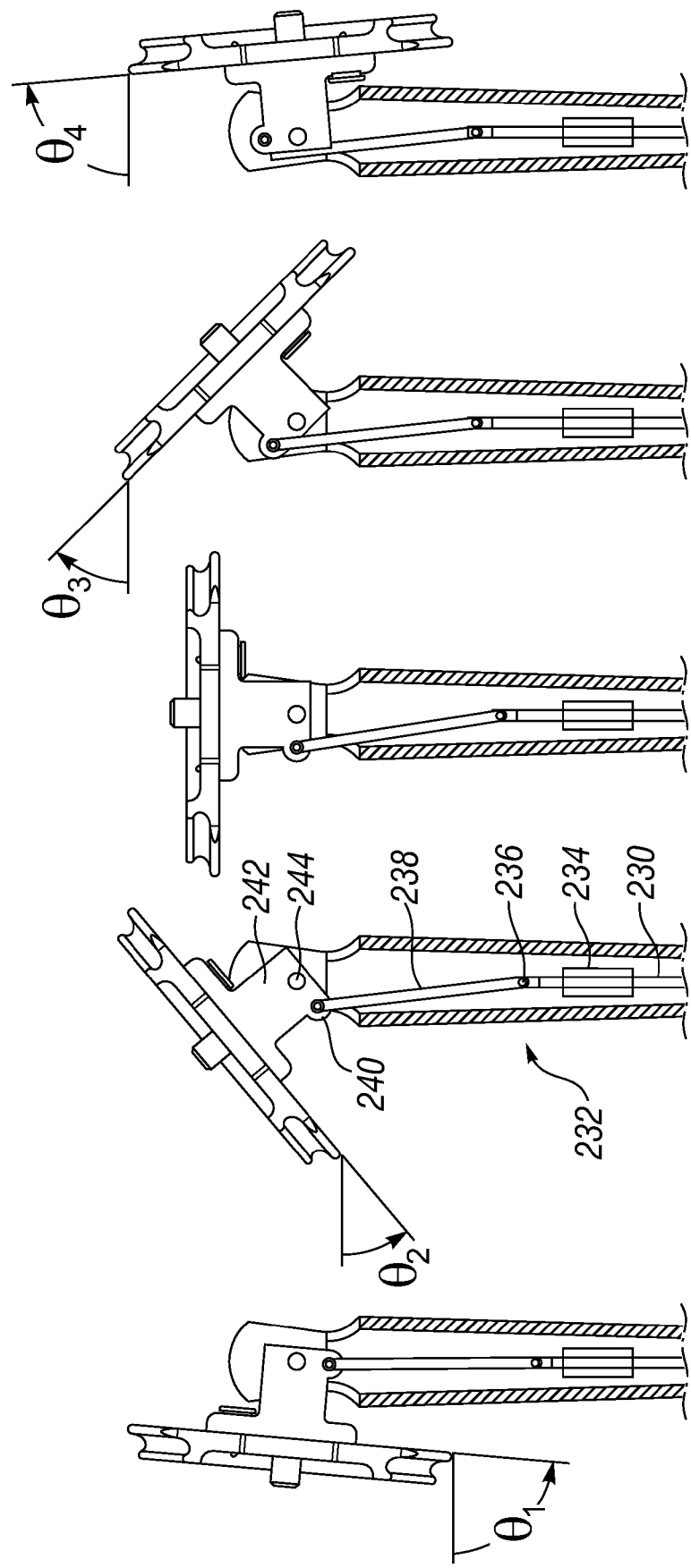

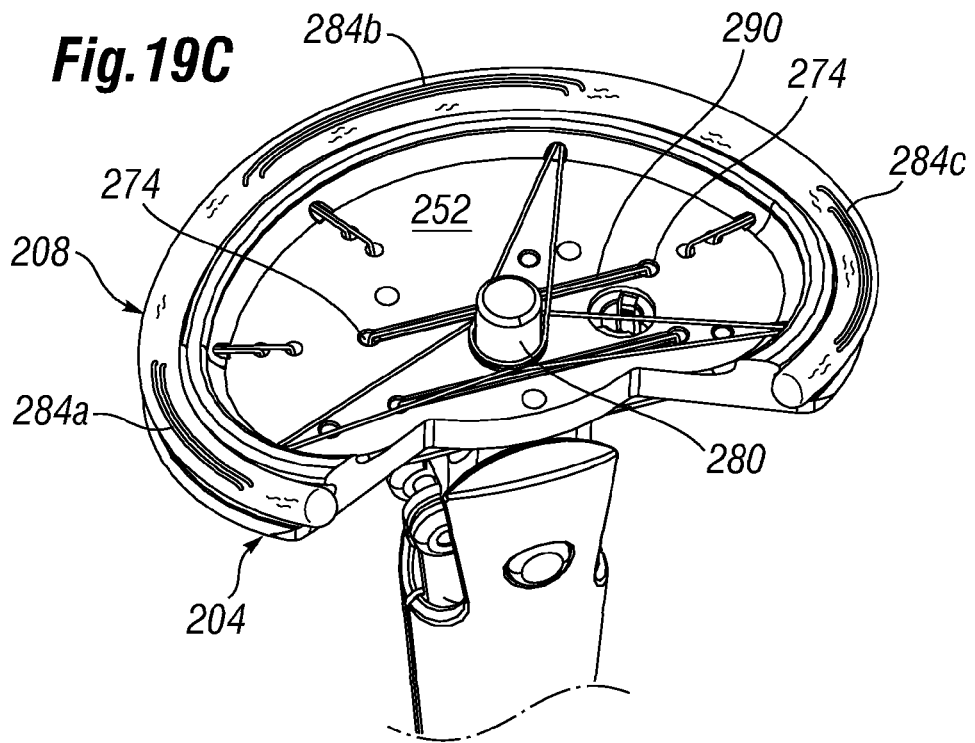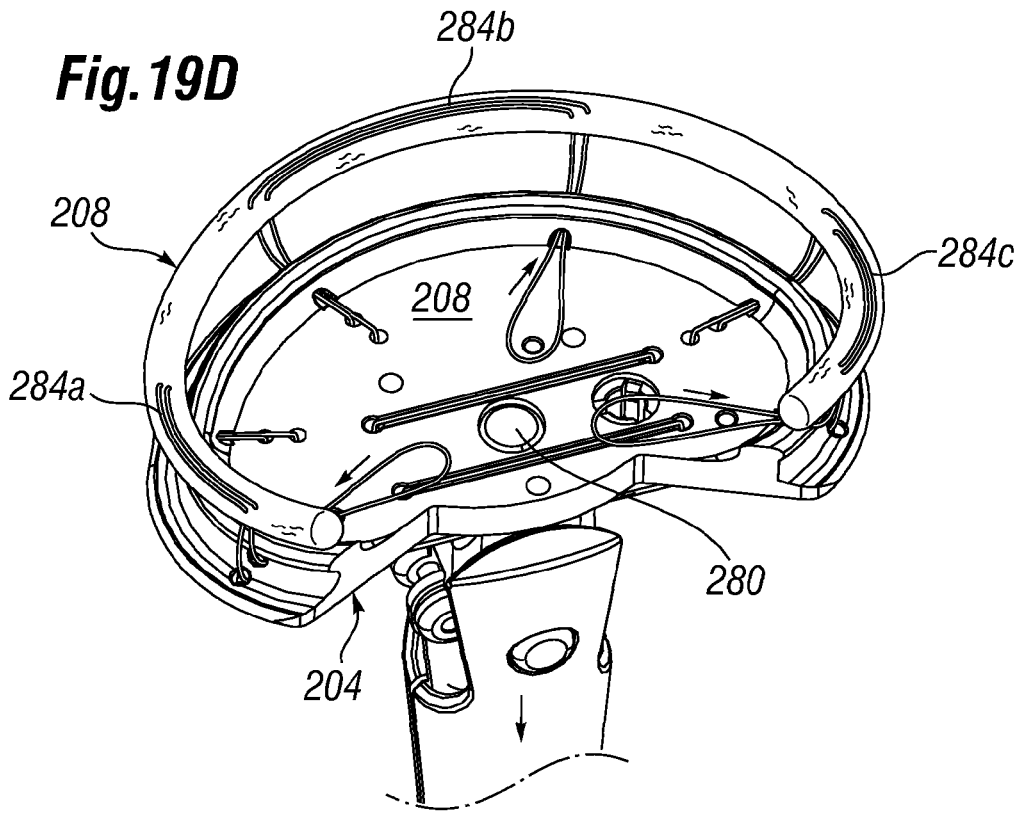

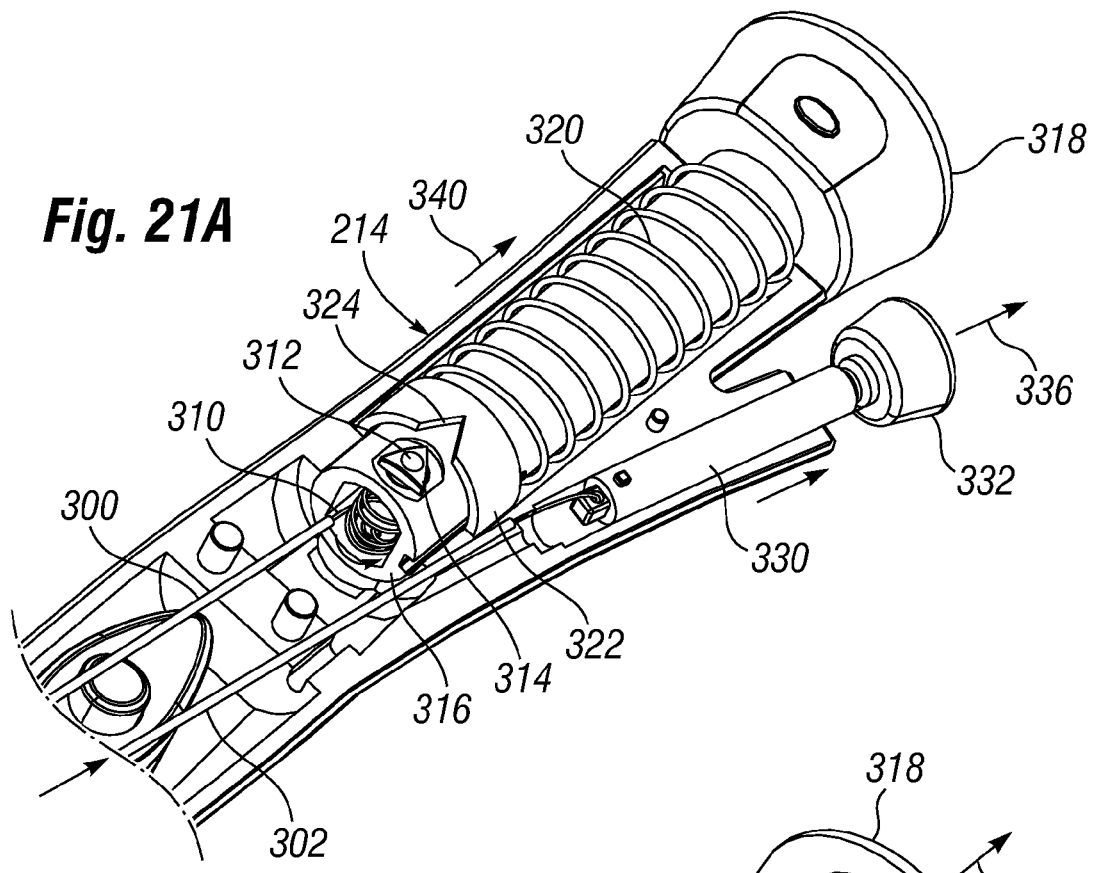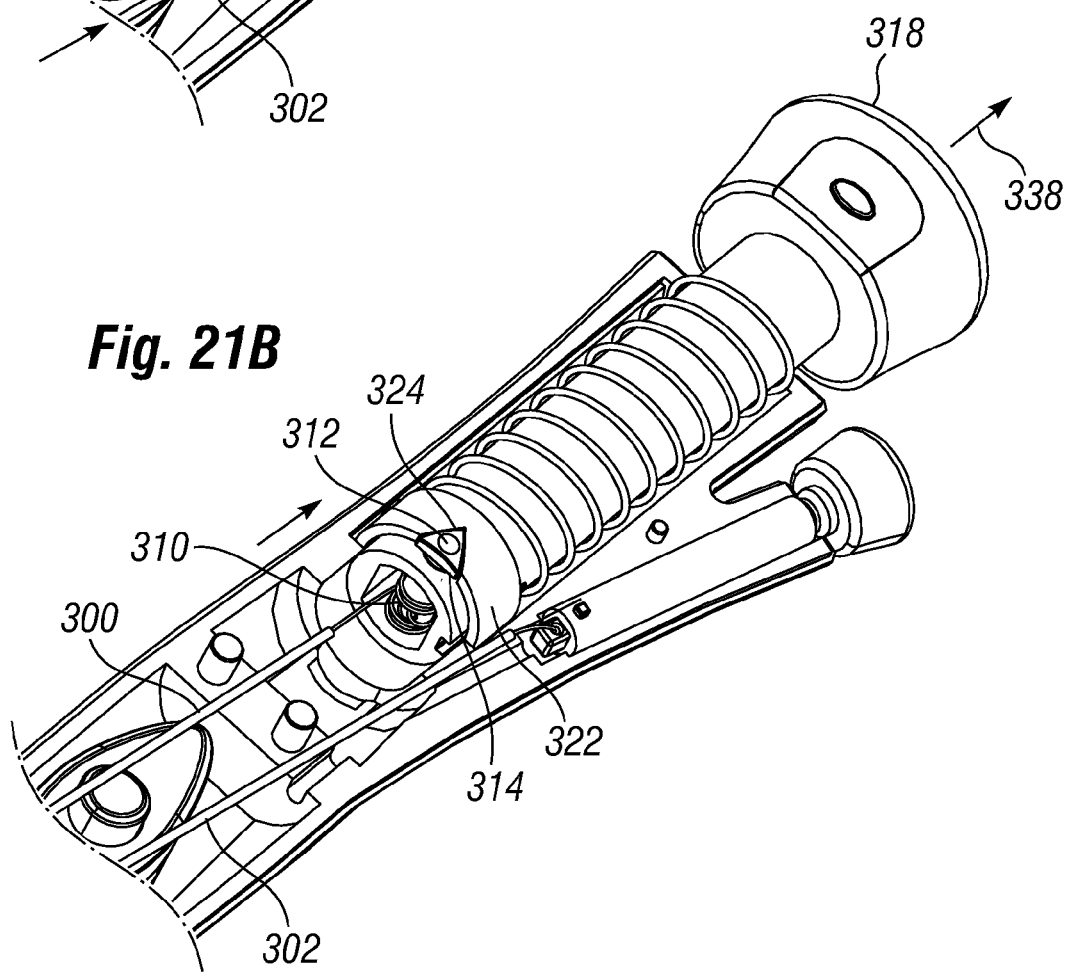

ACTIVE HOLDER FOR ANNULOPLASTY RING DELIVERY

CROSS REFERENCE TO RELATED APPLICATIONS

The present application claims priority to U.S. Provisional Patent Application No. 60/970,872, filed on Sep. 7, 2007, the disclosure of which is incorporated by reference herein in its entirety.

FIELD OF THE INVENTION

The present invention relates to a handle for delivering an implant and, more particularly, to a handle for delivering and facilitating implant of an annuloplasty ring.

BACKGROUND OF THE INVENTION

Heart valve disease is a widespread condition in which one or more of the valves of the heart fails to function properly. Diseased heart valves may be categorized as either stenotic, wherein the valve does not open sufficiently to allow adequate forward flow of blood through the valve, or incompetent, wherein the valve does not close completely, causing excessive backward flow of blood through the valve when the valve is closed. A heart valve may also be both stenotic and incompetent. Valve disease can be severely debilitating and even fatal if left untreated, particularly if the diseased valve is the mitral valve (between the left atrium and left ventricle) or the aortic valve (between the left ventricle and the aorta). According to recent estimates, more than 80,000 patients are diagnosed with aortic or mitral valve disease in U.S. hospitals each year.

Various surgical techniques may be used to repair a diseased or damaged valve. One repair technique which has been shown to be effective in treating incompetence, particularly of the mitral and tricuspid valves, is annuloplasty, in which the effective size of the valve annulus is contracted by attaching a prosthetic annuloplasty ring to an interior wall of the heart around the valve annulus. The annuloplasty ring comprises an inner substrate of a metal such as stainless or titanium, or a flexible material such as silicone rubber or Dacron cordage, covered with a biocompatible fabric or cloth to allow the ring to be sutured to the heart tissue. The annuloplasty ring may be stiff or flexible, may be split or continuous, and may have a variety of shapes, including circular, D-shaped, C-shaped, or kidney-shaped. Examples are seen in U.S. Pat. Nos. 4,917,698, 5,061,277, 5,290,300, 5,350,420, 5,104,407, 5,064,431, 5,201,880, and 5,041,130, which are incorporated herein by reference.

Using current techniques, most valve repair and replacement procedures require a gross thoracotomy, usually in the form of a median sternotomy, to gain access into the patient's thoracic cavity. A saw or other cutting instrument is used to cut the sternum longitudinally, allowing two opposing halves of the anterior or ventral portion of the rib cage to be spread apart. A large opening into the thoracic cavity is thus created, through which the surgical team may directly visualize and operate upon the heart and other thoracic contents. Alternatively, a thoracotomy may be performed on a lateral side of the chest, wherein a large incision is made generally parallel to the ribs, and the ribs are spread apart and/or removed in the region of the incision to create a large enough opening to facilitate the surgery.

Using such open-chest techniques, the large opening provided by a median sternotomy or right thoracotomy enables the surgeon to see the mitral valve directly through the left atriotomy, and to position his or her hands within the thoracic cavity in close proximity to the exterior of the heart for cannulation of the aorta and/or coronary arteries to induce cardioplegia, manipulation of surgical instruments, removal of excised tissue, and introduction of an annuloplasty ring or a replacement valve through the atriotomy for attachment within the heart. However, these invasive, open-chest procedures produce a high degree of trauma, a significant risk of complications, an extended hospital stay, and a painful recovery period for the patient. Moreover, while heart valve surgery produces beneficial results for many patients, numerous others who might benefit from such surgery are unable or unwilling to undergo the trauma and risks associated with open-chest procedures.

Annuloplasty ring prostheses are generally mounted on a holder assembly to facilitate their manipulation during the course of a surgical intervention and their implantation. Current holder assemblies are characterized by a number of drawbacks. A great majority of holders are configured with a rigid handle and a fixed orientation of the holder body or prosthesis carrier relative to the handle. Such a mechanical limitation does not allow the surgeon to orient the holder body relative to the handle in order to optimize the delivery of the prosthesis to the implant site. Some holder assemblies have been configured with malleable handles in an attempt to alleviate this drawback. However, such malleable handles are generally difficult to reshape in different bent configurations once they have been initially bent. Some holder assemblies have introduced shape memory alloys, such as Nitinol, for the material of the handle. Handles made from Nitinol that would be bent during the surgical procedure would resume their straight unbent shape after being exposed to sterilization temperatures. However, Nitinol handles are expensive and may be too easy to bend out of desired shape when the cardiac prosthesis mounted on end of such handles is exposed to tissue or suture loads during the surgical intervention.

In view of actual and perceived drawbacks associated with current annuloplasty techniques, there is a need for a less invasive approach and improved handle.

SUMMARY OF THE INVENTION

In one aspect, the present application discloses a holder for delivering an annuloplasty ring, comprising a template having a peripheral edge sized to receive an annuloplasty ring. A plurality of sutures attach the annuloplasty ring to the template, and the holder includes a handle having a pivot on which the template pivots to a variety of angles with respect to the handle. A ring detachment mechanism detaches the sutures attaching the annuloplasty ring to the template, and is remotely actuated from the handle. Also, a pivoting mechanism in the handle pivots the template.

The pivoting mechanism may include a gear train or a pulley system. In a preferred embodiment, the pivoting mechanism includes a push/pull rod linearly movable within the handle and connected to an eccentric projection of a pivot member on which the template mounts. The holder may further include a locking mechanism in the handle that permits a user to fix the angle of the template with respect to the handle. Desirably, the pivoting mechanism enables approximately 180° of rotation of the template.

The ring detachment mechanism may include hot wires, blades or a pull wire that sever the sutures attaching the annuloplasty ring to the template. Preferably, the ring detachment mechanism includes a pull wire, and the plurality of sutures attaching the annuloplasty ring to the template loop around a release pin movable in a bore in the template, the pull wire being connected to and able to displace the release pin to detach the annuloplasty ring from the template. In one embodiment, the release pin is movable in a bore in the template between an extended position around which the plurality of sutures loop to attach the annuloplasty ring to the template, and a retracted position that frees the suture loops to detach the annuloplasty ring from the template. Preferably, the holder further include a plurality of sutures attaching the handle to the template. A handle detachment mechanism for detaching the sutures attaches the handle to the template, and is remotely actuated from the handle.

Another aspect of the present application is a holder for delivering an annuloplasty ring comprising a proximal handle and a template mounted on the distal end of the handle having a peripheral edge sized to receive an annuloplasty ring. A source of illumination mount on the handle and is directed toward the template. The source of illumination is desirably mounted at the end of a malleable wire extending along the handle, wherein a portion of the handle is also malleable. An optic lens may also be mounted on the handle directed toward the template, and a viewer mounted at a proximal end of the handle permits a user to visualize the template through the lens.

A further aspect herein is a holder for delivering an annuloplasty ring that comprises a proximal handle and a template mounted on the distal end of the handle having a peripheral edge sized to receive an annuloplasty ring. An optic lens mounts on the handle and is directed toward the template, and a viewer mounted at a proximal end of the handle permits a user to visualize the template through the lens.

Another holder for delivering an annuloplasty ring disclosed herein includes a template having a peripheral edge sized to receive an annuloplasty ring, and a plurality of sutures attaching the annuloplasty ring to the template. A handle attaches to the template, and a ring detachment mechanism detaches the sutures attaching the annuloplasty ring to the template, and is remotely actuated from the handle. The ring detachment mechanism may includes hot wires, blades or a pull wire that sever the sutures attaching the annuloplasty ring to the template.

Preferably, the plurality of sutures attaching the annuloplasty ring to the template loop around a release pin movable in a bore in the template, and the pull wire connects to and displaces the release pin to detach the annuloplasty ring from the template. In one embodiment, the release pin is movable in a bore in the template between an extended position around which the plurality of sutures loop to attach the annuloplasty ring to the template, and a retracted position that frees the suture loops to detach the annuloplasty ring from the template. The holder further may include a pull wire in the handle connected on a distal end to the release pin and on a proximal end to a ring release button in the handle. A user may displace the release pin from the extended position to the retracted position by pulling the ring release button. The pull wire may connect on its proximal end to a pulley mounted to translate with the ring release button, wherein the pulley is free to rotate unless the user pulls the ring release button.

BRIEF DESCRIPTION OF THE DRAWINGS

Features and advantages of the present invention will become appreciated as the same become better understood with reference to the specification, claims, and appended drawings wherein:

FIG. 1 is a perspective view of an exemplary active annuloplasty ring holder;

FIG. 1A is a close-up perspective view of a distal end of the holder of FIG. 1 showing a pivoting annuloplasty ring template;

FIGS. 2A and 2B are front and side elevational views of the holder of FIG. 1;

FIGS. 3A-3C are close-up side elevational views of the distal end of the holder of FIG. 1 showing the template in several possible angular orientations;

FIG. 4 is a perspective exploded view of the exemplary active annuloplasty ring holder of FIG. 1;

FIG. 5 is a perspective assembled view of the holder of FIG. 1;

FIG. 6 is a perspective view of another exemplary active annuloplasty ring holder;

FIGS. 6A and 6B are close-up perspective views of a distal end of the holder of FIG. 6 showing a pivoting annuloplasty ring template;

FIGS. 7A and 7B are front and side elevational views of the holder of FIG. 6;

FIG. 8 is a perspective exploded view of the exemplary active annuloplasty ring holder of FIG. 6;

FIG. 9 is a perspective assembled view of the holder of FIG. 6;

FIG. 10 is a perspective view of the distal end of a further exemplary annuloplasty ring holder illustrating a mechanism for remotely detaching the annuloplasty ring from the holder that uses hot wires;

FIG. 10A is a close-up schematic view of the detaching operation of the hot wires of the holder of FIG. 10;

FIG. 13 is a side view of an annuloplasty ring holder having a source of illumination;

FIG. 14 is a side view of an annuloplasty ring holder having both a source of illumination and means for visualization;

FIGS. 15A and 15B are perspective and front elevational views of an alternative active annuloplasty ring holder;

FIGS. 18A-18E are longitudinal sectional views of the distal end of the ring holder of FIG. 15A showing a number of positions in which an annuloplasty ring template may be pivoted;

FIGS. 19A-19D are perspective views of the annuloplasty ring template of the holder of FIG. 15A showing a mechanism for securing and detaching an annuloplasty ring around the template;

FIGS. 21A and 21B are perspective views of the proximal end of the handle with a portion removed to show operation of both ring and handle release actuators therein;

DETAILED DESCRIPTION OF THE PREFERRED EMBODIMENTS

Figure 11:
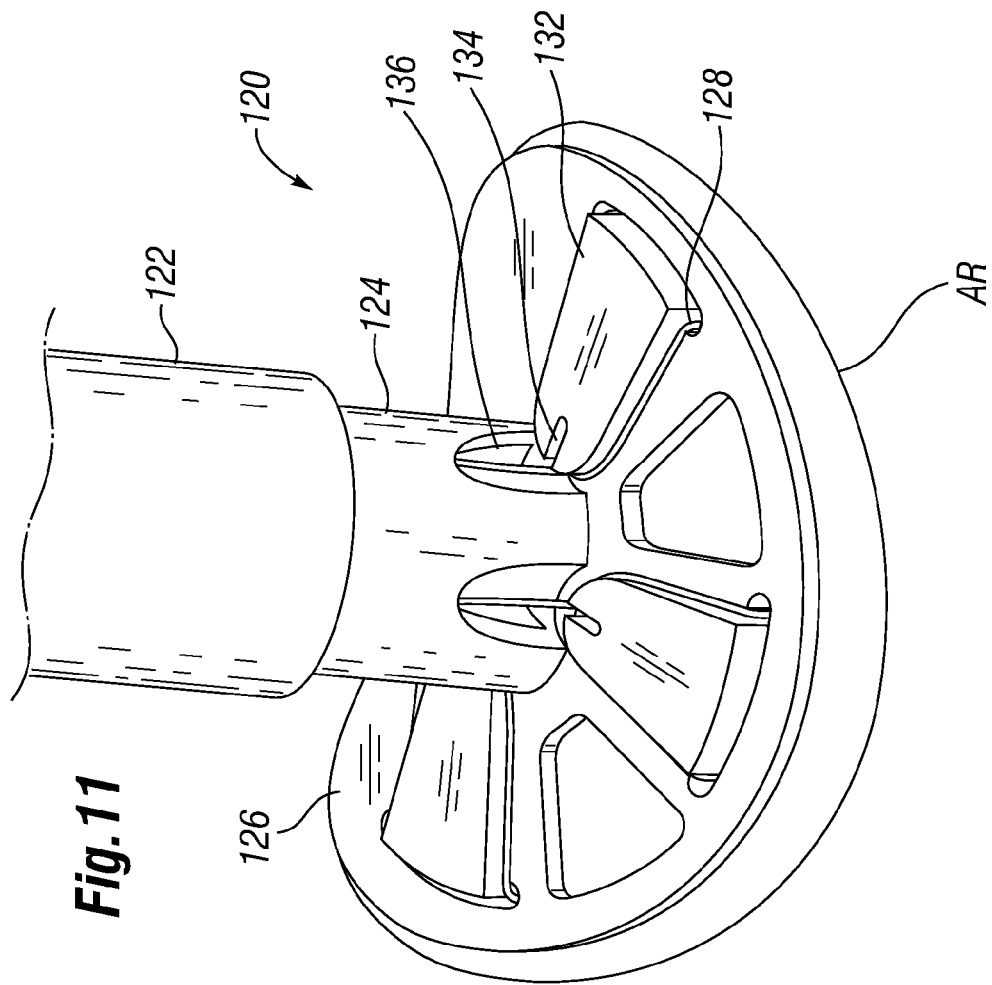
FIG. 11 is a perspective view of the distal end of a further exemplary annuloplasty ring holder illustrating a mechanism for remotely detaching the annuloplasty ring from the holder that uses severing blades.

Annuloplasty rings for valve repair are provided to surgeons with the holder to help facilitate the implantation of the ring in a human heart. The holder typically comprises a handle on the distal end of which is provided a template for mounting the annuloplasty ring. The handle may be designed to permit the surgeon to angle the template into a desired orientation. The template is rigid and has an outer peripheral edge in the shape of the annuloplasty ring. The rigid template helps maintain the desired form of the ring during this suturing process. The preferred method of mounting an annuloplasty ring to a template is using sutures threaded through the suture-permeable ring and attached to the template. In this context, "suture" refers to any biocompatible flexible filament that has sufficient strength to hold the ring in place around the template.

The surgeon delivers the ring to the implantation site on the template and sutures the ring into place prior to removing the template. After implantation, by severing each attaching suture, the template is pulled free from the ring and removed from the implantation site. Although, such holders are useful for open-chest procedures but are generally ill-suited for delivering rings through small incisions such as those used in less-invasive surgical or percutaneous procedures.

An active annuloplasty ring holder well-suited for delivering rings through small incisions and also having features as yet unavailable, and having the following advantages is disclosed:
1. The holder and ring section can be folded or pivoted to the side allowing them to align longitudinally with the handle and enter the patient's chest through a small incision.
2. The handle includes a mechanism that can be operated remotely, e.g., from outside the patient's body, to sever sutures fastening the ring to the holder, thereby detaching the ring from the holder, without the need to introduce a scalpel into the heart, thus avoiding the risk associated with such introduction.
3. The handle has a built-in light source for better visualization of the ring inside the heart.
4. The handle has an optical means of visualizing the inside of the heart from the proximal end of the handle.

Each of the above features can be implemented individually, or in combination with the other features.

With reference to FIGS. 1 and 1A, an exemplary active annuloplasty ring holder 20 comprises a proximal handle 22 having a hub 24 on a distal end on which a template 26 pivotally mounts. Although not shown, the template 26 is adapted to receive and secure thereon an annuloplasty ring around its periphery. In the illustrated embodiment, the template 26 is designed for delivering a mitral annuloplasty ring, and as such has a modified oval shape with the majority being convex and one side somewhat linear. The convex side receives the posterior aspect of the mitral annuloplasty ring, while the more linear side receives the anterior aspect of a continuous ring, or in the case of a discontinuous, C-shaped ring, no part of the ring extends along the linear side.

As mentioned, the template 26 pivots about the hub 24 via a pivoting mechanism 28, shown in more detail below with respect to FIG. 4. The handle 22 includes a proximal grip 30 and a malleable section 32 that extends between the grip and the hub 24. A rotation wheel 34 preferably actuated with the user's thumb projects outward about midway along the grip 30. Rotation of the wheel 34 causes pivoting movement of the template 26, as will be described.

FIGS. 2A and 2B are front and side elevational views of the holder 20 of FIG. 1. In an exemplary embodiment, the overall length A of the holder 20 is between 200-250 mm, and preferably 230 mm. The malleable section 32 has a length B of between 80-120 mm, and preferably about 100 mm.

FIGS. 3A-3C are close-up side elevational views of the distal end of the holder 20 of FIG. 1 showing the template 26 in several possible angular orientations. FIG. 3A shows the template 26 oriented in a typical implant position with the plane of the template perpendicular to the longitudinal axis of the hub 24. If the hub 24 is aligned with the rest of the handle 22, the template 26 is also perpendicular to the handle. FIG. 3A illustrates the template 26 at 0°, FIG. 3B shows the template at an angle of −45°, while FIG. 3C shows the template at an angle of 90°. Desirably, the pivoting mechanism 28 enables the template 26 to be pivoted up to 180° through its range of motion.

FIG. 4 is a perspective exploded view, and FIG. 5 a perspective assembled view, of the exemplary active annuloplasty ring holder 20 of FIG. 1 illustrating the various moving parts. In particular, the pivoting mechanism 28 comprises the aforementioned rotation wheel 34 journaled for rotation within the hollow grip 30. The rotation wheel 34 has a pulley 35 around which runs an elongated flexible transmission, such as a cord or belt 36. The belt 36 passes alongside a malleable stylet 38 within the handle 22 and into a hollow space within the hub 24. The belt 36 then passes around a second pulley 40 which is journaled for rotation about a pivot 42 in the hub 24. A key 44 rigidly affixed to the pulley 40 fits closely within a recess 46 on the underside of the template 26. Upon rotation of the wheel 34, the belt conveys rotational movement to the pulley 40, which in turn pivots the template 26 via the connection of the key 44 and recess 46. In this way, the user can easily pivot the template 26 using a thumb or finger on the rotational wheel 34. A spring 48 with relatively tight coils surrounds the belt 36 and stylet 38 to provide protection for the belt without sacrificing malleability.

FIG. 6 is a perspective view of another embodiment of an active annuloplasty ring holder 60 of the that comprises a proximal handle 62 having a hub 64 on a distal end on which a template 66 pivotally mounts. Although not shown, the template 66 is adapted to receive and secure thereon an annuloplasty ring around its periphery. In the illustrated embodiment, the template 66 is designed for delivering a mitral annuloplasty ring, and as such has a modified oval shape with the majority being convex and one side somewhat linear.

As mentioned, the template 66 pivots about the hub 64 via a pivoting mechanism 68, shown in more detail below with respect to FIGS. 6A, 6B and 8. The handle 62 includes a proximal grip 70 and a malleable section 72 that extends between the grip and the hub 64. A rotation knob 74 extends from the proximal end of the grip 70. Rotation of the knob 34 about the handle axis causes pivoting movement of the template 66, as will be described.

FIG. 8 is a perspective exploded view, and FIG. 9 a perspective assembled view, of the active annuloplasty ring holder 60 of FIG. 6 illustrating the various moving parts. In particular, the pivoting mechanism 68 comprises the aforementioned rotation knob 74 journaled for rotation on the proximal end of the hollow grip 70. The rotation knob 74 rigidly connects to an elongated shaft 76 that passes alongside a malleable stylet 78 within the handle 62 and terminates at a distal drive bevel gear 80. The bevel gear 80 engages a driven bevel gear 82 which is journaled for rotation about a pivot 84 in the hub 64. A key 86 rigidly affixed to the driven bevel gear 82 fits closely within a recess 88 on the underside of the template 66. Upon rotation of the knob 74, the shaft 76 conveys rotational movement to the drive bevel gear 80, which in turn rotates the driven bevel gear 82, and in turn the template 66 via the connection of the key 86 and recess 80. In this way, the user can easily pivot the template 66 using two fingers on the rotational knob 74. A spring 90 with relatively tight coils surrounds the shaft 76 and stylet 78 to provide protection without sacrificing malleability. In one embodiment, the shaft 76 comprises a coil of material so as to enable bending while still being capable of applying torque to the gear train.

FIG. 10 is a perspective view of the distal end of a further embodiment of an annuloplasty ring holder 100 illustrating a mechanism for remotely detaching the annuloplasty ring AR from the holder. As in the earlier embodiments, the holder 100 includes a proximal handle 102 having a hub 104 on the distal end, and the template 106 connected to the hub 104. The remote detachment mechanism may be utilized by itself in a conventional holder/template configuration, or may be coupled with any of the template pivoting mechanisms as described above.

The annuloplasty ring AR attaches around the arcuate periphery of the template 106 via a plurality of attachment sutures 108. Preferably, there are three loops of attachment sutures 108 relatively evenly spaced around the template 126. In a preferred embodiment, each of the attachment sutures 108 loops through a portion of the body of the suture-permeable ring AR and up over a groove provided in a guide 112. The guides 112 desirably comprise small steps or blocks projecting upward from a top surface 114 of the template 106. A hot wire 116 extends radially outward from within the hub 104 and loops around each one of the attachment suture loops 108. The wire 116 may be insulated except for a section which loops around the suture 108.

At an appropriate time, such as after the annuloplasty ring AR has been translated into its implant position but prior to tying implant knots, the wire 116 may be energized by a circuit passing through the handle 102 so that it heats up and cuts through the attachment suture 108. A battery and actuation button are desirably incorporated into the handle 102, and wires with some slack to enable bending or pivoting connect to the hot wires 116. FIG. 10A is a close-up schematic view of the detaching operation of the hot wires 116. In this way, each of the attachment sutures 108 can be simultaneously remotely severed at the guide 112. One or both ends of the severed attachment sutures 108 are secured to the template 106 so that the user can remove the template and all of the attachment sutures from the ring AR at the same time. In one embodiment, the hot wires 116 are printed onto a circuit board that forms a part of the template 106.

Figure 11A:
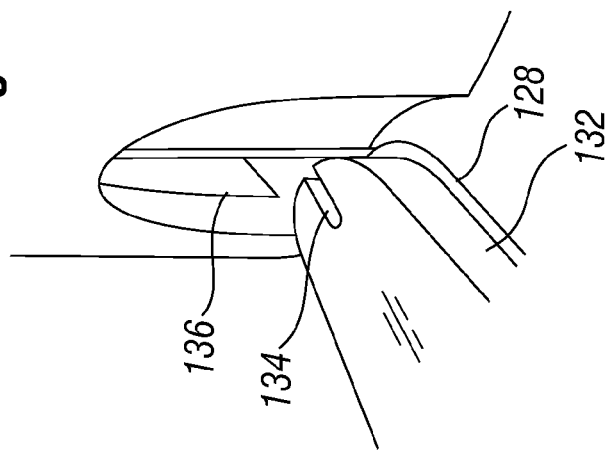
FIG. 11A is a close-up schematic view of the detaching operation of the severing blades of the holder of FIG. 11.

FIGS. 11 and 11A are perspective views of the distal end of a further exemplary annuloplasty ring holder 120 illustrating an alternative mechanism for remotely detaching the annuloplasty ring AR from the holder. Again, the holder 120 includes the handle 122, hub 124, and template 126. The template 126 may be fixed in a perpendicular orientation with respect to the handle 122, or may be capable of pivoting as described above. The attachment sutures 128 desirably extend radially inward around a guide 132 having a slot 134. A cutting blade 136 arranged to translate within the hub 124 lines with each slot 136. At the desired time, the cutting blades 136 simultaneously translate downward through the slots 134 to sever the attachment sutures 128. Although the mechanism for actuating the cutting blade 136 is not shown, it may comprise a simple pushrod extending through the handle that simultaneously displaces the three blades 36. Alternatively, a pull wire may be used.

Figure 12:
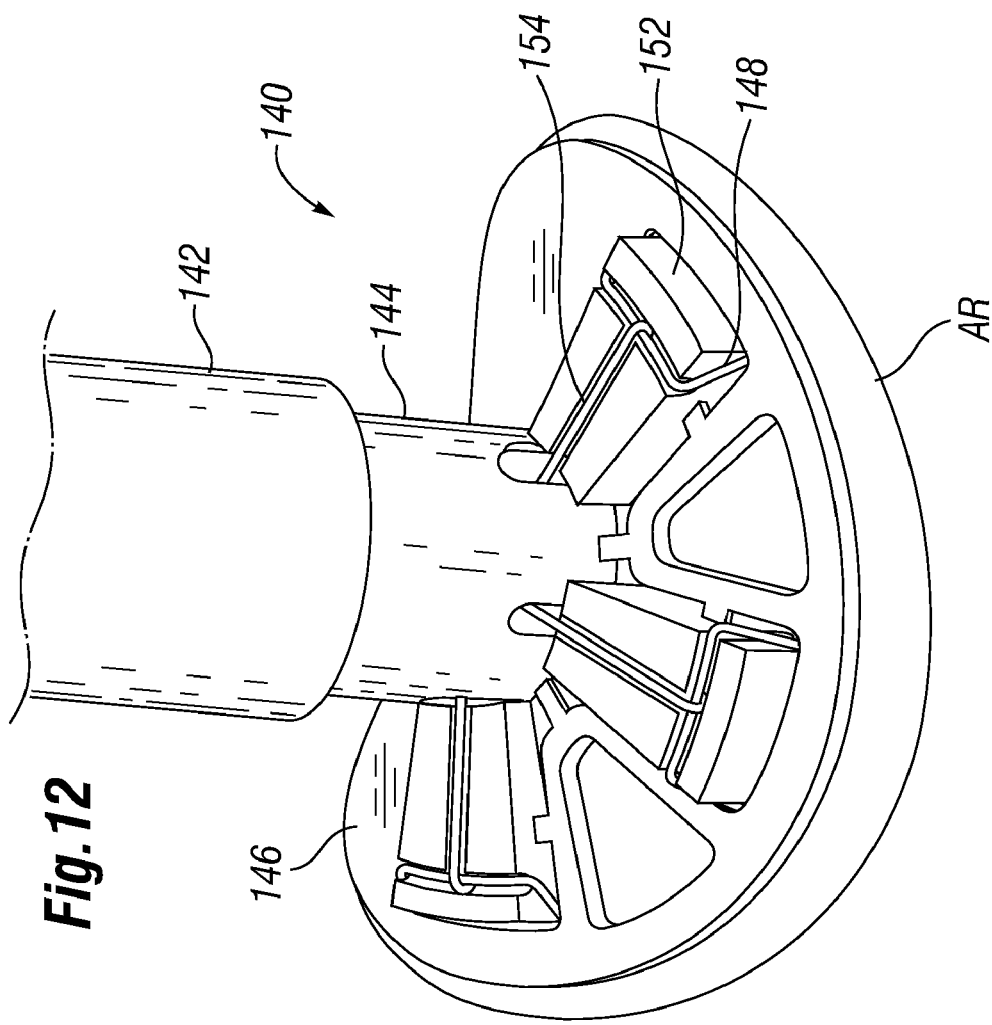
FIG. 12 is a perspective view of the distal end of a further exemplary annuloplasty ring holder illustrating a mechanism for remotely detaching the annuloplasty ring from the holder that uses pull wires.
Figure 12A:
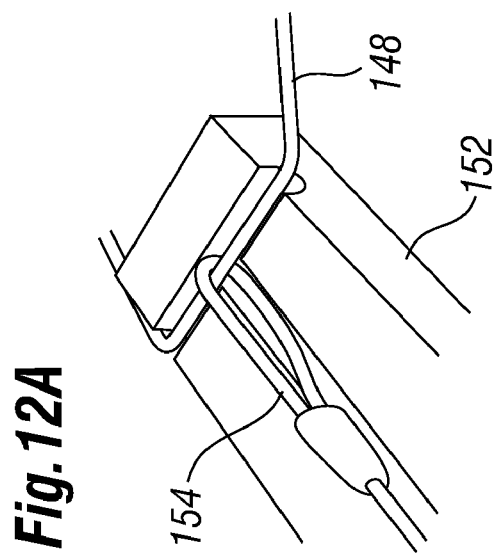
FIG. 12A is a close-up schematic view of the detaching operation of the pull wires of the holder of FIG. 12.

FIG. 12 is a perspective view of the distal end of a further exemplary annuloplasty ring holder 140 showing a mechanism for remotely detaching the annuloplasty ring AR from the holder. Again the holder 140 includes the handle 142, hub 144, and template 146. The template 146 may be fixed in a perpendicular orientation with respect to the handle 142, or may be capable of pivoting as described above. As in the embodiment of FIG. 10, each of the attachment sutures 148 passes over a template guide 152. A pull wire 154 for each of the loops of the attachment sutures 148 extends outward from the hub 144. FIG. 12A is a close-up of the detaching operation of the pull wires 154. Namely, the pull wire 154 is arranged to apply concentrated stress to each of the attachment sutures 148 and sever it at the template guide 152. The mechanism for actuating the pull wires 154 is not shown, although a reel/knob taking up the proximal ends of each of the pull wires 154 and actuated through mechanical advantage is a likely configuration.

To improve visualization, it is desirable to add illumination by embedding a light source on the distal end of the holders described herein. To energize the light source, a battery or other power source may be incorporated into the handle. FIG. 13 is a side view of one illuminated annuloplasty ring holder 160. The holder 160 includes the proximal handle 162 and distal template 164. A light source 166, such as an LED, forms the terminal end of a malleable wire 168 and projects toward the template 164. The malleable wire 168 may be closely held against the bendable handle 162 so that the light source 166 always points toward the template 164.

In addition, it may also be desirable to add optics so as to visualize the inside of the heart from the proximal end of the handle. FIG. 14 is a side view of an annulus ring holder 170 having both a source of illumination and means for visualization. The holder 170 includes a proximal handle 172 and distal template 174. A light source 176 on the end of the malleable wire 178 may be energized using a battery within the handle 172. In addition, an optic lens 180 arranged adjacent the light source 176 connects through an optic fiber 182 to a proximal viewer 184. The viewer 184 includes an ocular device that permits the user to easily and rapidly see the area around the annuloplasty ring template 174 during an implant operation.

Figure 15B:
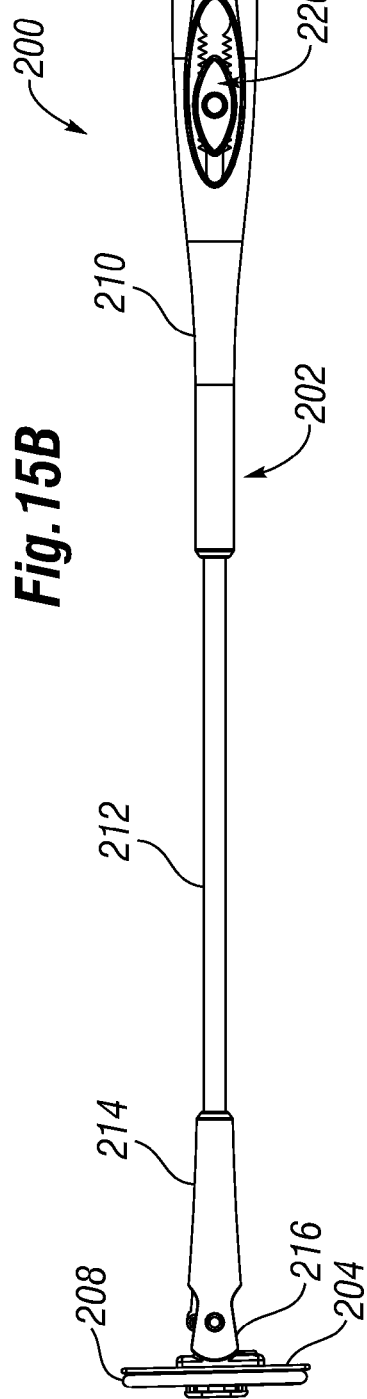

FIGS. 15A and 15B illustrate an alternative active annuloplasty ring holder 200. The holder 200 comprises an elongated handle 202 and an annuloplasty ring template 204 pivotally attached to a distal end thereof. The template 204 defines a peripheral edge 206 sized to receive an annuloplasty ring 208. As will be explained in detail below, a plurality of sutures attach the annuloplasty ring 208 to the template 204.

FIG. 15B shows that the elongated handle 202 comprises three primary sections: a proximal section 210, a middle section 212, and a distal section 214. The proximal section 210 consists of a hollow housing, typically molded plastic, which is larger in diameter than the other two sections and has an ergonomic shape to facilitate grasping by the surgeon. The middle section 212 is an elongated hollow tube through which control elements extend, as will be described below. The distal section 214 is also formed by a hollow housing that terminates in a bifurcated yoke 216. Like the embodiments described above, the overall length of the holder 200 is between 200-250 mm, and preferably about 230 mm. The middle section 212 has a length of between 80-120 mm, and preferably about 100 mm, and may be malleable as described above, but is preferably relatively rigid to enable functioning of pull/push rods passing therethrough. The materials used in the handle sections, as well as the other elements of the holder 200, may be any suitable biocompatible plastic or metal.

Figure 16A:
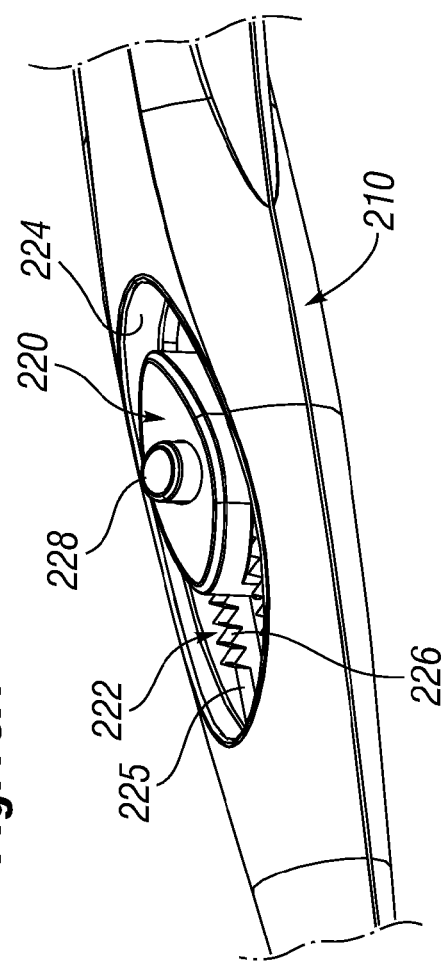
FIG. 16A is a close-up perspective view of an actuating button on a handle of the ring holder of FIG. 15A.
Figure 16B:
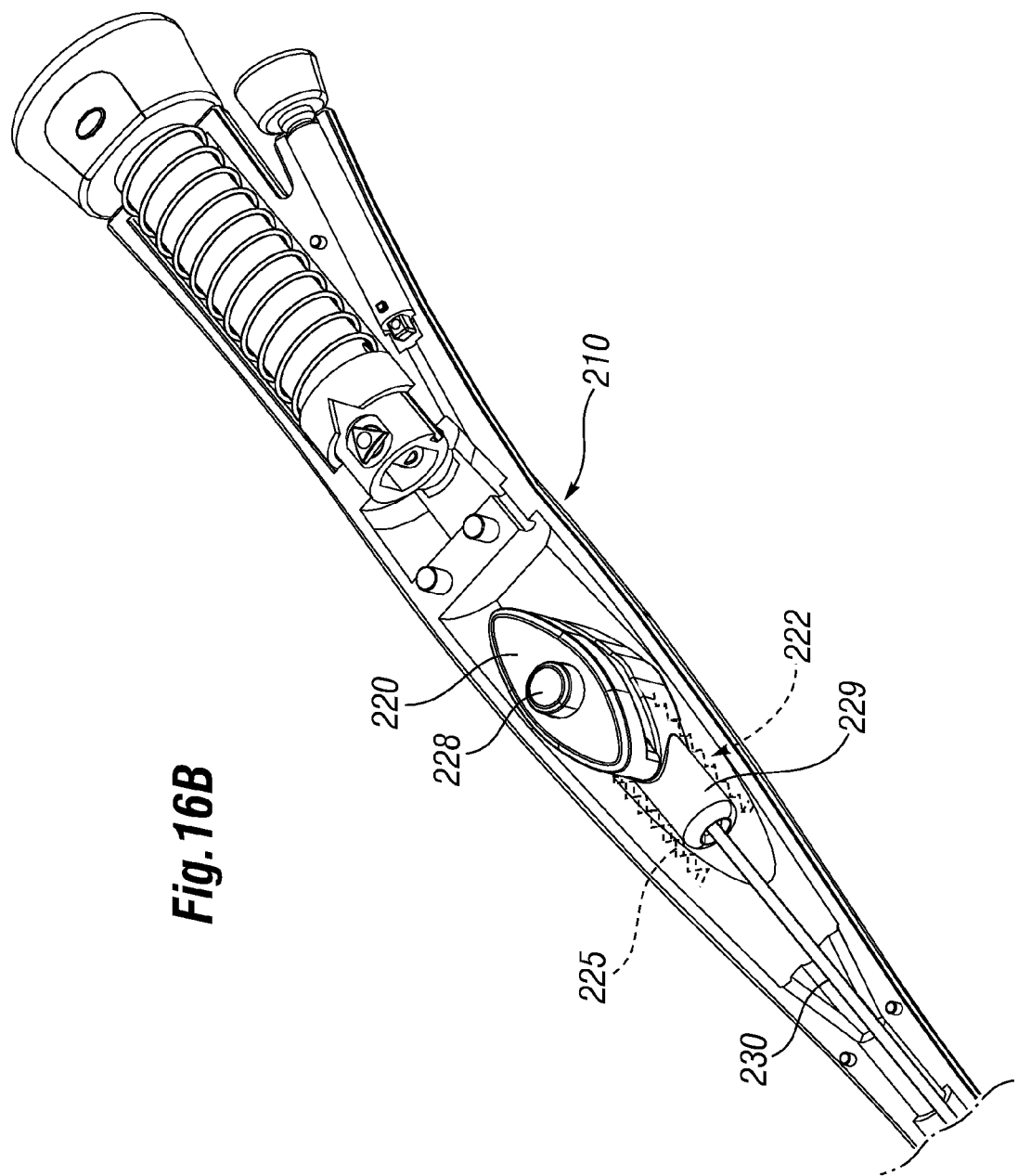
FIG. 16B is a sectional perspective view of the actuating button with a portion of the handle removed to illustrate a locking mechanism therein.

FIG. 16A is a close-up of a pivot actuator 220 and locking mechanism 222 on the proximal section 210 of the handle 202, while FIG. 16B shows a portion of the proximal section housing removed to illustrate certain internal components. The pivot actuator 220 translates linearly along the handle 202 to pivot the distal annuloplasty ring template 204. An exemplary pivoting mechanism will be described with respect to FIG. 17, although those skilled in the art will understand with reference to other embodiments described herein that there are other ways to pivot the template 204.

The locking mechanism 222 permits the user to fix the position of the pivot actuator 220, therefore fixing the angle of the template 204 with respect to the longitudinal axis of the handle 202. The handle 202 defines a recess 224 and a slot 225 within which the pivot actuator 220 translates. In the illustrated embodiment, the actuator 220 and recess 224 are substantially lenticular. A plurality of ratchet teeth 226 extend inward on both sides of the slot 225 and engage mating pawl or teeth (not shown) on the underside of the actuator 220. A small locking button 228 projecting upward from the top surface of the actuator 220 enables selective retraction of the mating pawl. Although the details of the locking button 228 are not shown, an exemplary embodiment includes a lever or cam that retracts the mating pawl(s) when the locking button is depressed, and a spring element that biases the locking button upward so as to automatically lock the position of the actuator 220. The user can depress the locking button 228 in order to slide the actuator 220. A small tube 229 fixed with respect to the actuator 220 receives and anchors to a push/pull rod 230 that is part of a pivoting mechanism 232 described below. Although a linear actuator 220 is shown, other actuators like rotating knobs or hinged triggers may be utilized, and the particular motion of the actuator may be modified.

Figure 17:
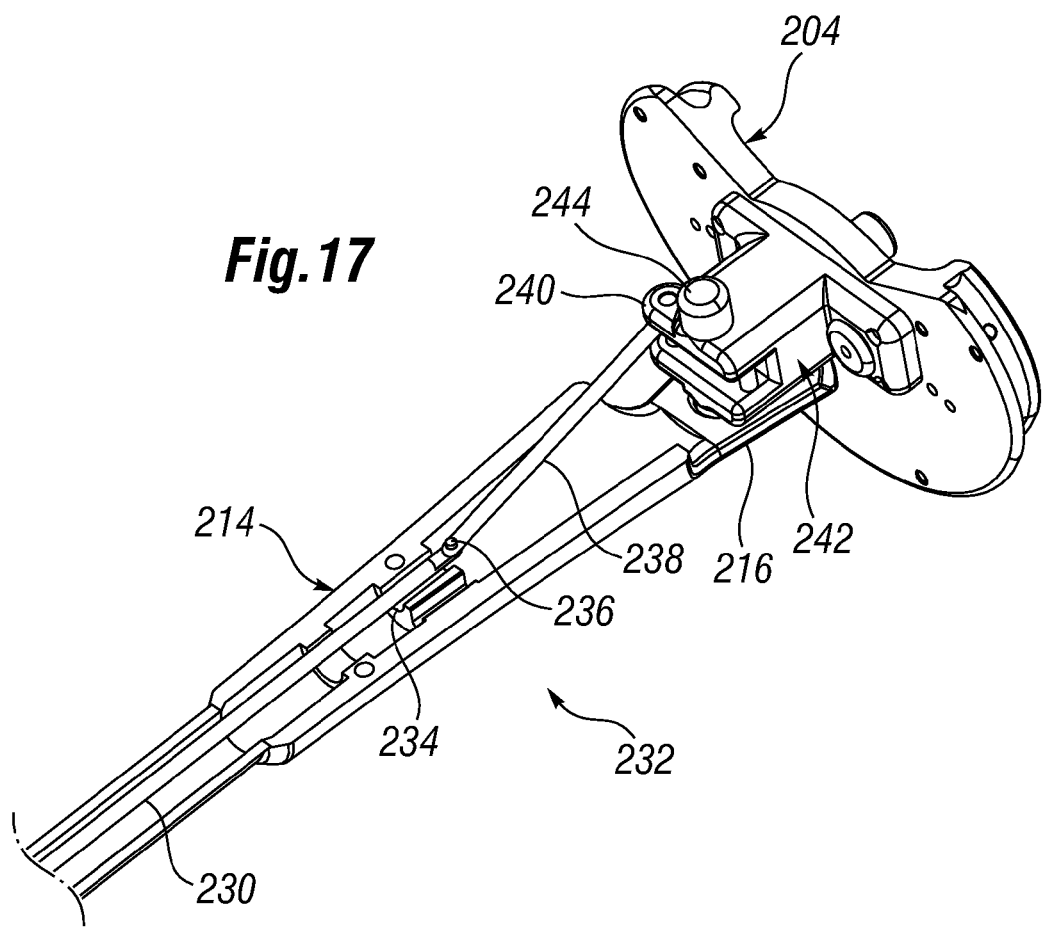
FIG. 17 is a sectional perspective view of a distal segment of the ring holder of FIG. 15A with a portion of the handle removed to illustrate an inner template pivoting mechanism.

FIG. 17 illustrates the distal segment of the ring holder 200 of FIG. 15A with a portion of the handle 202 removed to illustrate the internal template pivoting mechanism 232. At its proximal end, the pivoting mechanism 232 includes the push/pull rod 230 that translates linearly within the lumen of the handle 202. Although not shown, the push/pull rod 230 firmly attaches to and translates with the pivot actuator 220. Push/pull rod 230 travels through a linear bearing 234 within the handle 202 for support. A hinge 236 connects the push/pull rod 230 to a link arm 238. The distal end of the link arm 238 is hingedly connected to an eccentric projection 240 of a pivot member 242, also seen in FIG. 19A. The pivot member 242, in turn, mounts for rotation within the yoke 216 at the distal end of the handle 202. Specifically, the pivot member 242 includes a pair of opposed pivot pins 244 that are received within a pair of through holes in each arm of the yoke 216. Linear translation of the push/pull rod 230 displaces the link arm 238 which, through its hinged connection to the eccentric projection 240, rotates the pivot member 242 about the common axis of the pivot pins 244.

FIGS. 18A-18E show a number of positions in which an annuloplasty ring template 204 may be pivoted by operation of the pivoting mechanism 232. In an equilibrium position in FIG. 18C, the template 204 is oriented perpendicular to the axis of the handle 202. In the illustrated embodiment, the template 204 has a planar configuration but templates that are non-planar may also be utilized. For instance, rings and corresponding templates that have three dimensions with one or more bows out of a reference plane are becoming more prevalent, and may be mounted on the active holder disclosed herein.

In any event, the active holder 200 desirably permits pivoting rotation of the template 204 within a range of up to about 180°. FIG. 18A shows the template 204 pivoted counterclockwise an angle $\theta_1$ of nearly −90° from the horizontal, FIG. 18B shows an angle $\theta_2$ of about −45°, FIG. 18D shows a clockwise rotation to an angle $\theta_3$ of about 45°, and FIG. 18E shows a farther clockwise rotation to an angle $\theta_4$ of nearly 90°. Each of these orientations may be useful during delivery of annuloplasty ring. Furthermore, rotating the template 204 reduces the horizontal dimension of the active holder 200 and permits the insertion through relatively smaller spaces than would be the case without rotation.

The active holder 200 further includes a mechanism for remotely detaching the annuloplasty ring 208 from the template 204. In a conventional system, the annuloplasty ring attaches to the template via a plurality of sutures which are tied to the template and cross over one or more cutting guides. The surgeon severs the sutures at the cutting guides to release the annuloplasty ring, which requires scalpel access to the template at the site of implantation. The holder disclosed herein provides a remote detaching mechanism that desirably can be operated from the proximal end of the handle 202.

FIGS. 19A-19D illustrate the annuloplasty ring template 204 and elements of a mechanism for securing and easily detaching an annuloplasty ring around the template. As mentioned above, the template 204 generally defines a planar body 252 and has a peripheral edge 206 sized to receive an annuloplasty ring 208 (see FIG. 15A). The illustrated template 204 is sized and shaped to receive a mitral annuloplasty ring, and as such has a generally oval- or D-shaped periphery.

Various exemplary annuloplasty rings may be utilized in conjunction with the holders disclosed herein, and preferably comprise a flexible, stiff, or deformable support ring covered by a fabric or mesh suitable for suturing the annuloplasty ring to heart tissue. The support ring may be a biocompatible metal such as stainless steel or titanium or a flexible material such as silicone rubber or Dacron cordage, depending upon the structural and performance characteristics desired in the ring. The overlying fabric or mesh may be a polyester knit fabric, polyester velour cloth, expanded polytetrafluoroethylene, or other biocompatible porous material with sufficient structural integrity to resist tearing when a suture is passed through it and secured to the heart. The holders disclosed herein may be adapted for use with any of the various commercially available annuloplasty rings, including the rigid Carpentier-Edwards Classic® ring, the semi-flexible Carpentier-Edwards Physio®, or the flexible ring Cosgrove-Edwards® annuloplasty ring, all available from Edwards Lifesciences, Irvine, Calif. Other rings include the SCULPTOR or DURAN rings available from Medtronic, Inc. of Minneapolis, Minn., the PUIG MASSANA ring available from Sorin Biomedica of Salaggia, Italy, or the BIFLEX Ring available from St. Jude Medical, Inc. of St. Paul, Minn.

The holders disclosed herein are configured to hold annuloplasty rings of various shapes and sizes. Specifically, the present holders may be adapted for holding D-shaped split annuloplasty rings, D-shaped continuous annuloplasty rings, or C-shaped split or open annuloplasty rings. The embodiment of the template 204 illustrated in FIG. 19A has a C-shaped configuration with the peripheral edge 206 extending approximately two thirds of the way around the template body 252. Other annuloplasty ring shapes may also be used with the holder, including kidney-shaped, saddle-shaped racetrack-shaped, semicircular, circular, and others. Mitral rings and corresponding holders typically have orifice sizes that range in even millimeter increments from 24 mm to 40 mm, as measured across the major axis. In some cases, the annuloplasty ring may be flexible and may have a shape in a natural, unstressed condition which is different than the shape of holder. For example, a circular ring could be held by a D-shaped holder. In this way, the ring conforms to the shape of holder and is held in the shape it will be in when secured within the heart. The ring may also be malleable so that it may be bent into the shape of the holder and/or reshaped by the surgeon at the time of implantation within the heart.

Figure 19A:
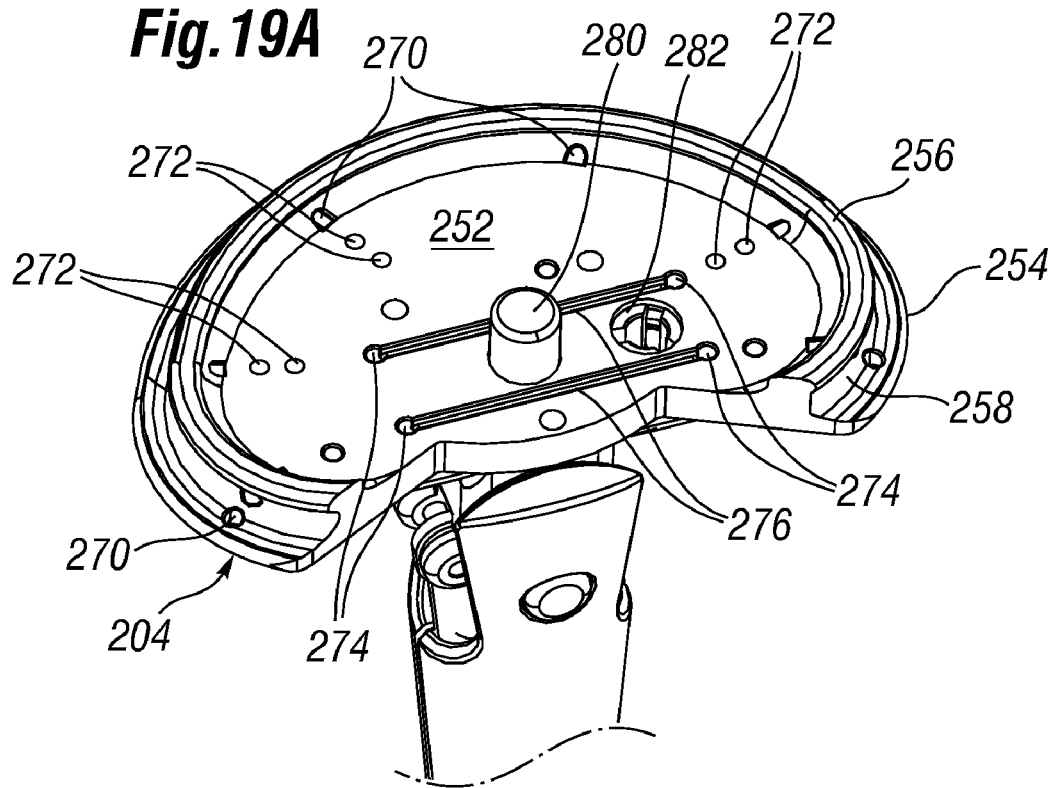
Figure 19B:
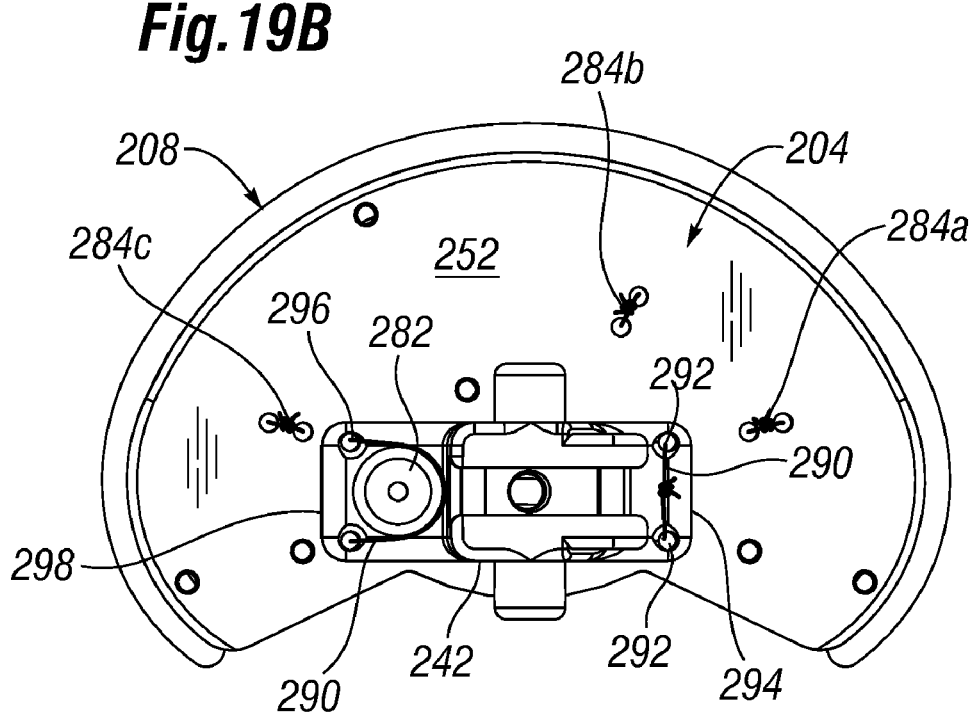

The peripheral edge 206 of the exemplary template 204, as seen in FIGS. 19A and 19B, comprises a proximal lip 254, a distal rail 256, and an outwardly directed channel depression 258 therebetween. As seen in FIG. 15A, the proximal lip 254 forms a radially outward extension of the flat proximal side of the template body 252. The distal rail 256 projects distally from the underside of the template body 252 and is radially inset from the outer edge of the proximal lip 254. The channel 258 is therefore defined between the substantially perpendicular lip 254 and rail 256, although all of the respective surfaces are smoothly curved such that the channel substantially mirrors the tubular outer periphery of typical annuloplasty rings.

The template 204 features a number of holes and depressions for threading and guiding sutures therethrough. Some of the sutures are used to secure an annuloplasty ring within the channel 258 on the peripheral edge 206, while some of the sutures are used to secure the handle 202, and more specifically the pivot member 242, to the template 204. FIG. 19A shows the under- or distal side of the template 204 while FIG. 19B shows the top or proximal side. To better illustrate the suture holes/grooves, an annuloplasty ring 208 and connecting sutures are only shown in FIG. 19B.

A series of outer holes 270 extend through from the channel 258 to the radially inner side of the rail 256. The annuloplasty ring 208 resides in the channel 258 when connected, and as will be seen, a plurality of sutures pass outward through the rail 256, through the suture-permeable ring, and back inward through the rail. Just inward from three of the outer holes 270 are located pairs of template body holes 272. The holes 272 extend all the way through the template body 252, and can be seen on the proximal side in FIG. 19B. Four rectangularly spaced handle holes 274 also pass completely through the template body 252. Two linear grooves 276 in the distal face of the template body 252 connect two pairs of the four handle holes 274.

Still with reference to FIG. 19A, a ring release pin 280 in an extended position projects distally through a bore (not numbered) in the template body 252, located generally centrally and between the linear grooves 276. As will be seen, the release pin 280 is movable in the bore between the extended position in FIG. 19A and a retracted position shown in FIG. 19D. Also seen in FIG. 19A is the bottom end of a handle release pin 282, which will be described below.

Now with reference to FIGS. 19B and 19C, an exemplary arrangement of sutures for mounting the annuloplasty ring 208 to the template is shown. Three double ring attachment sutures 284a, 284b, 284c thread downward from the proximal side of the template 204, outward through the ring 208, and inward to loop around the ring release pin 280, as seen in FIG. 19C. Each double suture 284a, 284b, 284c passes through the template 204 and ring 208 as two parallel threads with free ends that diverge to pass through different template body holes 272 and knot together on the proximal side of the template body 252, as seen in FIG. 19B. More specifically, the sutures 284a, 284b, 284c are routed outward from the template body holes 272 across the distal face of the template body 252 and pass outward through the outer holes 270 in the distal rail 256 (see FIG. 19A). The sutures 284a, 284b, 284c are threaded through or along portions of the ring 208, as seen in dashed line in FIG. 19C, and then pass inward through outer holes 270 in the distal rail 256 and loop around the ring release pin 280. The closed end of each suture 284a, 284b, 284c therefore loops around the release pin 280 in its extended position, as seen in FIG. 19C to attach the annuloplasty ring to the template.

FIG. 19D shows the template 204 being pulled free of the annuloplasty ring 208. This step occurs after the ring 208 has been anchored to the annulus under repair. That is, the surgeon uses the handle 200 to advance the ring 208 into position along a plurality of pre-attached suture loops around the annulus. Each of the anchoring sutures are then tied off on the proximal side of the ring 208. The template 204 maintains the ring 208 in a desired shape during the anchoring procedure. Once the ring is secured to the annulus, the surgeon remotely actuates the ring release pin 280 to displace it to its retracted position seen in FIG. 19D, with its distal end flush with or above the distal face of the template body 252. Movement of the pin 280 to the retracted position frees the suture loops 284a, 284b, 284c to detach the annuloplasty ring 208 from the template 204. That is, once the loops are free, the template 204 may be displaced proximally, and the free ends of each suture 284a, 284b, 284c that are tied to the template pull the closed loops from within their paths in the ring 208. This detachment step is seen occurring in FIG. 19D.

It should be noted that although the traditional parachute array of pre-attached anchoring sutures is desirably used to secure the annuloplasty ring 208 to the annulus, other anchoring means are possible without affecting the use of the exemplary active holder 200. For instance, the process may be expedited with the use of staples, or remote suturing methods. Any of the foregoing or other implantation methods may also be used.

The handle 202 is also detachably connected to the template 204, and may be remotely disconnected. With reference again to FIGS. 19A and 19B, two double threads 290a, 290b include free ends that are tied through holes 292 to one side flange 294 of the pivot member 242 of the handle 202 (shown removed in FIG. 19B for clarity). The double threads 290a, 290b pass downward through the two holes 292 in the flange 294 that align with two of the handle holes 274 in the template body 252. The double threads 290a, 290b then extend along the grooves 276 as seen in FIG. 19A and pass upward through the other pair of handle holes 274 and two aligned holes 296 in another flange 298 on the pivot member 242, as seen in FIG. 19B. The double threads 290a, 290b then loop around a projecting portion of the handle release pin 282.

Figure 20A:
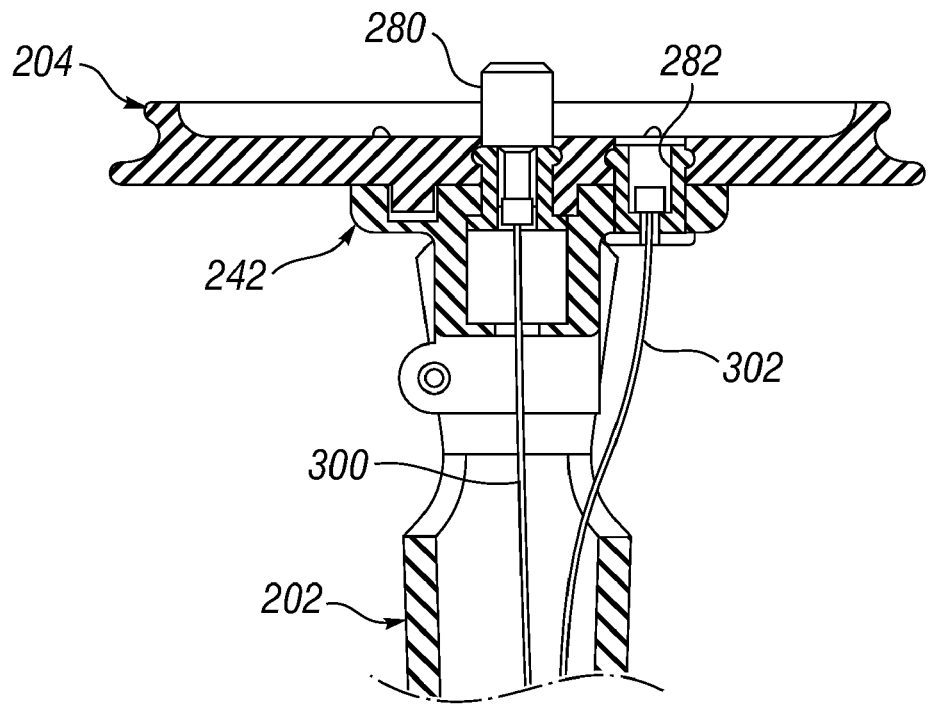
FIGS. 20A and 20B are longitudinal sectional views through the distal end of the holder and annuloplasty template of FIG. 15A illustrating the operation of two pull wires for releasing the annuloplasty ring and the handle, respectively, from the template.
Figure 20B:
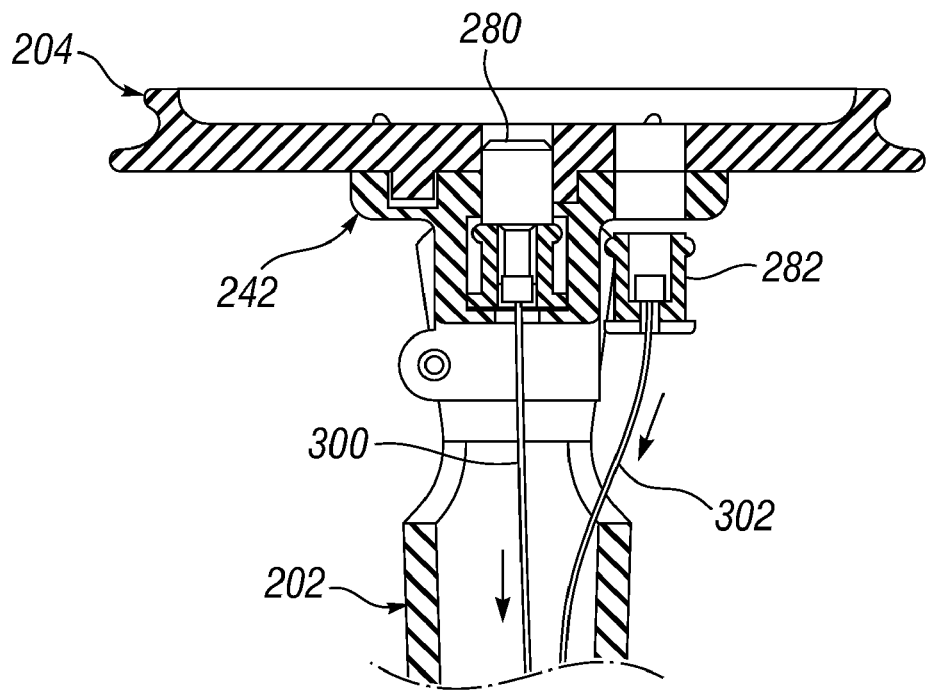

FIGS. 20A and 20B illustrate the distal end of the holder 200 and show the connection of two pull wires 300, 302 for, respectively, releasing the annuloplasty ring 208 and handle 202 from the template 204. A ring release pull wire 300 extends distally through the handle 202 and firmly connects to the ring release pin 280. The ring release pin 280 desirably includes cantilevered features (not numbered) on its exterior to engage mating features in the corresponding template bore and prevent inadvertent movement. Tension applied to the pull wire 300 will displace the release pin 280 from its extended position to its retracted position, and release the ring 208 from the template 204. It should be understood that the term "pull wire" refers to any biocompatible flexible filament that has sufficient strength to transmit the tension required to move the release pin 280.

The handle release pull wire 302 extends distally through the handle 202 and firmly connects to the handle release pin 282. The handle release pin 282 also desirably includes cantilevered features on its exterior to engage mating features in the corresponding template bore and prevent inadvertent movement. Tension applied to the pull wire 302 will displace the release pin 282 from its extended position to its retracted position, and release the handle 202 from the template 204.

FIGS. 21A and 21B show the proximal end of the handle 202 and operation of both ring and handle release actuators therein. A pulley mechanism 310 ensures that while the handle 202 is withdrawn from the template 204, the ring release pin 280 will not also be drawn back. Specifically, the ring release pull wire 300 travels through the handle and anchors to the shaft 312 of the pulley mechanism 310. The shaft 312 carries on one or both ends a triangular stop member 314. The pulley mechanism 310 mounts in the bore of a tubular sleeve 316 arranged to slide linearly within the housing of the handle distal section 214. A ring release button 318 caps the proximal end of the tubular sleeve 316. Between the pulley mechanism 310 and the ring release button 318, the housing 214 defines a larger bore in which is positioned a spring 320 in contact with a collar 322 having a triangular notch 324. The triangular notch 324 is shaped, sized, and aligned to mate with the triangular stop member 314 if the ring release button 318 and tubular sleeve 316 are displaced in a proximal direction. In the configuration of FIG. 21A the shaft 312 is free to rotate.

FIG. 21A also illustrates the handle release pull wire 302 as it travels through the handle 202 and anchors to the distal end of a handle release shaft 330 and button 332. Detachment of the handle 202 from the template 204 occurs by pulling the handle release button 332 as indicated by arrow 336, which applies tension to the handle release pull wire 302 and displaces the release pin 282 from its extended position to its retracted position, as seen in FIG. 20B.

Detachment of the ring 208 from the template 204 occurs by pulling the ring release button 318 as indicated by arrow 338 in FIG. 21B, which applies tension to the ring release pull wire 300 and displaces the release pin 280 from its extended position to its retracted position, as also seen in FIG. 20B. Pulling the ring release button 318 pulls the triangular stop member 314 into the triangular notch 324 of the collar 322, which prevents rotation of the shaft 312 and uncoiling of the pull wire 300 from the pulley mechanism 310.

If the surgeon wishes to just detach the handle 202 from the template 204, he or she can pull the handle release button 332 and then the entire handle 202, as indicated by arrow 340 in FIG. 21A. Because the triangular stop member 314 remains spaced from the triangular notch 324 the shaft 312 is permitted to uncoil from the pulley mechanism 310, which prevents undue tension being placed on the ring release pull wire 300.

Figure 22:
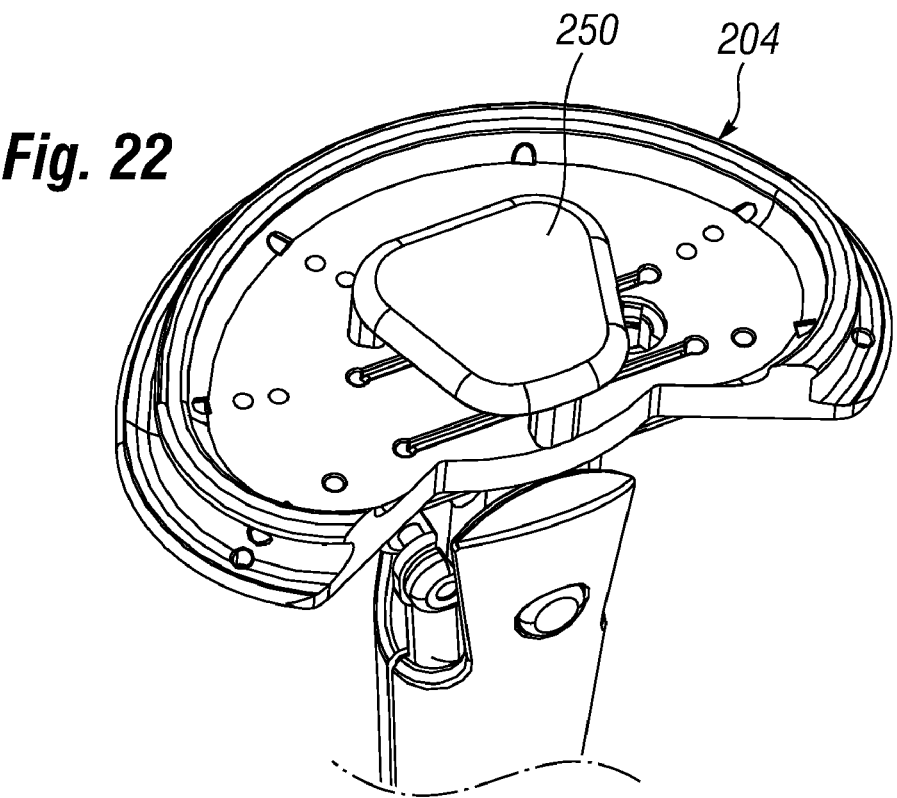
FIG. 22 is a distal perspective view of the annuloplasty ring template assembled with a release pin cover thereon.

FIG. 22 is a distal perspective view of the annuloplasty ring template 204 assembled with a release pin cover 250 thereon. The cover 250 prevents inadvertent deployment of the ring release pin 280 from its extended position to its retracted position, thereby protecting the assembly from accidental ring detachment. The cover 250 can be removed just before implantation of the ring 308.

Figure 23:
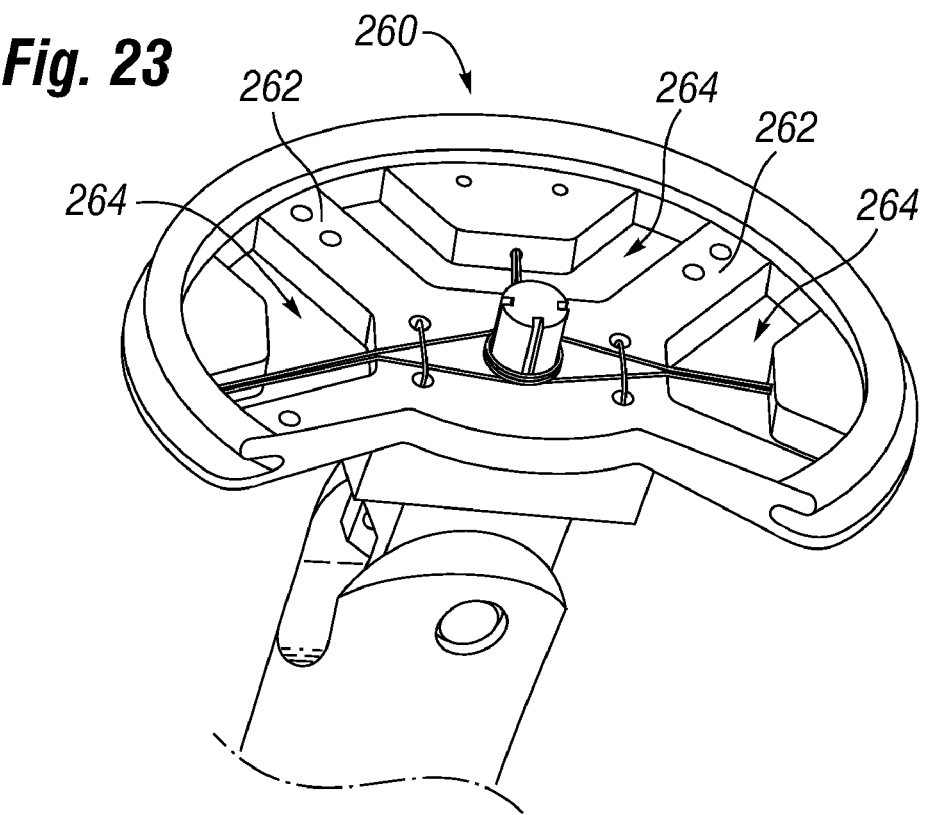
FIG. 23 is a distal perspective view of an alternative annuloplasty ring template similar to that of FIG. 15A but with spokes and windows for greater visibility.

FIG. 23 is a distal perspective view of an alternative annuloplasty ring template 260 similar to that of FIG. 15A but with spokes 262 and windows 264 for greater visibility. The windows 264 permit the surgeon to view the distal side of the assembly during the process of advancing the ring into implant position, and while the ring is anchored to the annulus. Preferably there are four spokes 262 and three windows 264, though other configurations are possible.

While the invention has been described in its preferred embodiments, it is to be understood that the words which have been used are words of description and not of limitation. Therefore, changes may be made within the appended claims without departing from the true scope of the invention.

What is claimed is:

1. A holder for delivering an annuloplasty ring, comprising:
    a template having a peripheral edge sized to receive an annuloplasty ring;
    a plurality of sutures attaching the annuloplasty ring to the template;
    a handle having a pivot on which the template pivots to a variety of angles with respect to the handle;
    a ring detachment mechanism for detaching the sutures attaching the annuloplasty ring to the template, the ring detachment mechanism being remotely actuated from the handle and including a release pin movable in a bore in the template between an extended position around which the plurality of sutures loop to attach the annuloplasty ring to the template and a retracted position that frees the suture loops to detach the annuloplasty ring from the template; and
    a pivoting mechanism in the handle for pivoting the template.

2. The holder of claim 1, wherein the pivoting mechanism includes a gear train.

3. The holder of claim 1, wherein the pivoting mechanism includes a pulley system.

4. The holder of claim 1, wherein the pivoting mechanism includes a push/pull rod linearly movable within the handle and connected to an eccentric projection of a pivot member on which the template mounts.

5. The holder of claim 1, further including a locking mechanism in the handle that permits a user to fix the angle of the template with respect to the handle.

6. The holder of claim 1, wherein the pivoting mechanism enables approximately 180° of rotation of the template.

7. The holder of claim 1, wherein the ring detachment mechanism includes a pull wire.

8. The holder of claim 7, wherein the pull wire connects to and displaces the release pin to detach the annuloplasty ring from the template.

9. The holder of claim 1, further including:
    a plurality of sutures attaching the handle to the template; and
    a handle detachment mechanism for detaching the sutures attaching the handle to the template, the detachment mechanism being remotely actuated from the handle.

10. A holder for delivering an annuloplasty ring, comprising:
    a template having a peripheral edge sized to receive an annuloplasty ring;
    a plurality of sutures attaching the annuloplasty ring to the template;
    a handle attached to the template; and
    a ring detachment mechanism for detaching the sutures attaching the annuloplasty ring to the template, the ring detachment mechanism being remotely actuated from the handle and including a release pin movable in a bore in the template between an extended position around which the plurality of sutures loop to attach the annuloplasty ring to the template and a retracted position that frees the suture loops to detach the annuloplasty ring from the template.

11. The holder of claim 10, further including:
an optic lens mounted on the handle and directed toward the template, and a viewer mounted at a proximal end of the handle that permits a user to visualize the template through the lens.

12. The holder of claim 11, further including:
a source of illumination mounted on the handle and directed toward the template.

13. The holder of claim 12, wherein the source of illumination is mounted at the end of a malleable wire extending along the handle, and wherein a portion of the handle is malleable.

14. The holder of claim 10, further including a pull wire in the handle connected on a distal end to the release pin and on a proximal end to a ring release button in the handle, such that a user may displace the release pin from the extended position to the retracted position by pulling the ring release button.

15. The holder of claim 14, wherein the pull wire connects on its proximal end to a pulley mounted to translate with the ring release button, wherein the pulley is free to rotate unless the user pulls the ring release button.

16. The holder of claim 10, further including:
a plurality of sutures attaching the handle to the template; and
a handle detachment mechanism for detaching the sutures attaching the handle to the template, the detachment mechanism being remotely actuated from the handle.

17. The holder of claim 10, further including:
a pull wire in the handle connected on a distal end to the release pin and on a proximal end to a ring release button in the handle, such that a user may displace the release pin from the extended position to the retracted position by actuating the ring release button; and
a handle detachment mechanism for detaching the handle from the template,
wherein the pull wire mounts in the handle in a manner that prevents application of tension sufficient to displace the release pin from the extended position to the retracted position when the handle detaches and is displaced away from the template unless the user actuates the ring release button.

18. The holder of claim 10, further including a pivoting mechanism in the handle for pivoting the template.

19. The holder of claim 18, further including a locking mechanism in the handle that permits a user to fix the angle of the template with respect to the handle.

20. The holder of claim 10, wherein each of the plurality of sutures is anchored at its free ends to the template and a mid-portion of each suture passes in two parallel threads outward through holes in the template and through the annuloplasty ring, and then inward through holes in the template to loop around the release pin.

21. The holder of claim 20, wherein the plurality of sutures are distributed around the template and the release pin is located generally centrally in the template.

22. The holder of claim 20, wherein the release pin projects beyond a distal face of the template in its extended position and the plurality of sutures each passes inward across the distal face of the template to loop around the release pin in its extended position.

23. The holder of claim 10, further including a removable release pin cover that prevents inadvertent deployment of the ring release pin from its extended position to its retracted position.

24. A holder for delivering an annuloplasty ring, comprising:
a template having a peripheral edge sized to receive an annuloplasty ring;
a plurality of sutures attaching the annuloplasty ring to the template;
a handle attached to the template; and
a ring detachment mechanism for detaching the sutures attaching the annuloplasty ring to the template, the ring detachment mechanism being remotely actuated from the handle, wherein the ring detachment mechanism includes a pull wire, and wherein the plurality of sutures attaching the annuloplasty ring to the template loop around a release pin movable in a bore in the template, and the pull wire connects to and displaces the release pin to detach the annuloplasty ring from the template.

25. The holder of claim 24, further including:
a plurality of sutures attaching the handle to the template; and
a handle detachment mechanism for detaching the sutures attaching the handle to the template, the detachment mechanism being remotely actuated from the handle.

26. The holder of claim 25, wherein the pull wire connects on a proximal end to a ring release button in the handle, such that a user may displace the release pin from the extended position to the retracted position by actuating the ring release button, wherein the pull wire mounts in the handle in a manner that prevents application of tension sufficient to displace the release pin from the extended position to the retracted position when the handle detaches and is displaced away from the template unless the user actuates the ring release button.

27. The holder of claim 26, wherein the pull wire connects on its proximal end to a pulley mounted to translate with the ring release button, wherein the pulley is free to rotate unless the user actuates the ring release button.

28. The holder of claim 24, further including a pivoting mechanism in the handle for pivoting the template.

29. The holder of claim 28, further including a locking mechanism in the handle that permits a user to fix the angle of the template with respect to the handle.

30. The holder of claim 24, wherein each of the plurality of sutures is anchored at its free ends to the template and a mid-portion of each suture passes in two parallel threads outward through holes in the template and through the annuloplasty ring, and then inward through holes in the template to loop around the release pin.

31. The holder of claim 30, wherein the plurality of sutures are distributed around the template and the release pin is located generally centrally in the template.

32. The holder of claim 30, wherein the release pin projects beyond a distal face of the template in its extended position and the plurality of sutures each passes inward across the distal face of the template to loop around the release pin in its extended position.

33. The holder of claim 24, further including a removable release pin cover that prevents inadvertent deployment of the ring release pin from its extended position to its retracted position.

* * * * *